(12) United States Patent
Lee et al.

(10) Patent No.: US 10,184,943 B2
(45) Date of Patent: Jan. 22, 2019

(54) MULTIPLE BIOMARKER SET FOR BREAST CANCER DIAGNOSIS, METHOD OF DETECTING THE SAME, AND DIAGNOSIS KIT FOR BREAST CANCER USING ANTIBODY AGAINST THE SAME

(71) Applicants: Bertis Co., Ltd., Seoul (KR); SNU R&DB FOUNDATION, Seoul (KR)

(72) Inventors: Heon Soo Lee, Seongnam-si (KR); Hye Seoung Shin, Seongnam-si (KR); Un-Beom Kang, Seoul (KR); Dong-Young Noh, Seoul (KR); Hyeong-Gon Moon, Seoul (KR)

(73) Assignee: BERTIS CO., LTD., Gabgnam-gu (KR)

( * ) Notice: Subject to any disclaimer, the term of this patent is extended or adjusted under 35 U.S.C. 154(b) by 122 days.

(21) Appl. No.: 14/383,392

(22) PCT Filed: Mar. 8, 2013

(86) PCT No.: PCT/KR2013/001911
§ 371 (c)(1),
(2) Date: Sep. 5, 2014

(87) PCT Pub. No.: WO2013/133675
PCT Pub. Date: Sep. 12, 2013

(65) Prior Publication Data
US 2015/0024960 A1    Jan. 22, 2015

(30) Foreign Application Priority Data

Mar. 8, 2012  (KR) .................... 10-2012-0023703

(51) Int. Cl.
*G01N 33/574* (2006.01)
*G01N 33/92* (2006.01)
*G01N 33/68* (2006.01)

(52) U.S. Cl.
CPC ... *G01N 33/57415* (2013.01); *G01N 33/6848* (2013.01); *G01N 33/92* (2013.01); *G01N 2333/705* (2013.01); *G01N 2333/70503* (2013.01); *G01N 2333/775* (2013.01); *G01N 2333/78* (2013.01); *G01N 2333/938* (2013.01); *G01N 2333/988* (2013.01); *G01N 2800/60* (2013.01)

(58) Field of Classification Search
None
See application file for complete search history.

(56) References Cited

U.S. PATENT DOCUMENTS

2007/0231909 A1  10/2007  Hunter
2010/0159492 A1   6/2010  Bergmann
2010/0173788 A1   7/2010  Goncalves et al.
2012/0109533 A1   5/2012  Kwon et al.

FOREIGN PATENT DOCUMENTS

JP     2009511915 A     3/2009
KR  10-2009-0079845 A   7/2009
KR  10-2010-0129457 A  12/2010
WO      02077176 A2   10/2002

OTHER PUBLICATIONS

Kim et al., J. Proteome Res., 2010, 9: 689-699.*
Sequence Alignment_SEQ ID No. 1.*
Sequence Alignment_SEQ ID No. 5.*
Sequence Alignment_SEQ ID No. 6.*
Sequence Alignment_SEQ ID No. 10.*
Pietrowska et al., J. Translational Med., 2009, 7: 2-13.*
Kokoglu et al., Cancer Biochem. Biopphys, 1994, 14: 133-136; Abstract.*
Senchenko et al., PLoS One, 2011, 6: 1-11.*
Luo et al., Mol. Biol., 2005, 29: 233-244.*
Sequence alignment_7 (Sep. 6, 2016).*
Sequence alignment_8 (Sep. 6, 2016).*
Sequence alignment_9 (Sep. 6, 2016).*
Seman et al., Biochem. Cell. Biol., 1986, 64: 999-1009.*
Fless et al., J. Lipid Res., 1985, 26: 1224-1229.*
Reblin et al., Atherosclrosis, 1999, 145: 71-79.*
Wang Aikang and Liu Chuangfeng, "Distribution of fibronectin in benign and malignant breast diseases", Ningbo Medicines, Nov. 2, 1999, vol. 11, Issue 2, pp. 59-60.
Yuxia Fan et al., "Detection and identification of potential biomarkers of breast cancer", J Cancer Res Clin Oncol, 2010, vol. 136, pp. 1243-1254.
Albina Zoltowska, et al., "Neural Cell Adhesion Molecule in Breast, Colon and Lung Carcinomas", Short Communication, 2001, pp. 171-174, vol. 49.

(Continued)

*Primary Examiner* — Ileana Popa
(74) *Attorney, Agent, or Firm* — McDonnell Boehnen Hulbert & Berghoff LLP

(57) ABSTRACT

The present invention relates to a biomarker set for diagnosing breast cancer comprising two or more protein markers of: apolipoprotein C1, apolipoprotein (a), neural cell adhesion molecule L1-like protein, carbonic anhydrase 1, and fibronectin; a method for detecting the biomarker set in a blood sample through a multiple reaction monitoring; a kit for diagnosing breast cancer comprising antibodies specific to each of the proteins of the biomarker set; and a method for detecting proteins of the marker set in a blood sample through an antigen-antibody binding reaction. The method for detecting the protein marker set in a blood sample by the MRM method or antigen-antibody binding reaction and the diagnostic kit can provide very high accuracy and sensitivity in comparison with the diagnosis method using a single marker and can very conveniently diagnose breast cancer using blood from patients, thereby being effectively used for early diagnosis of breast cancer.

3 Claims, 6 Drawing Sheets
Specification includes a Sequence Listing.

(56) References Cited

OTHER PUBLICATIONS

Narges K. Tafreshi, et al., "Noninvasive Detection of Breast Cancer Lymph Node Metastasis Using Carbonic Anhydrases IX and XII Targeted Imaging Probes", Clinical Cancer Research, 2011, pp. 207-219, vol. 18, No. 1.

E Ruiz-Garcia, et al., "Gene expression profiling identifies Fibronectin I and CXCL9 as candidate biomakers for breast cancer screening", British Journal of Cancer, 2010, pp. 462-468, vol. 102.

Richard Tuli, et al., "Diagnosis, Treatment, and Management of Breast Cancer in Previously Augmented Women", The Breast Journal, 2006, pp. 343-348, vol. 12, No. 4.

Shawn R. Clinton, et al., "A Comparative Study of Four Serological Tumor Markers for the Detection of Breast Cancer", Journal of the Mississippi Academy of Sciences, Apr. 2002, pp. 126-133, vol. 47, No. 2.

SR Clinton, et al., "A comparative study of four serological tumor markers for the detection of breast cancer", Biomed Sci Instrum, 2003, 1 page, vol. 37, (Abstract only).

Zhao Rui, et al., "Use of serological proteomic methods to find biomarkers associated with breast cancer", Proteomics, 2003, pp. 433-439, vol. 3.

Gyorgy Soletormos, et al., "Serological tumor markers for monitoring breast cancer", Danish Medical Bulletin, Nov. 2001, pp. 229-255, vol. 48, No. 4.

Marit Westerterp, et al., "Apolipoprotein C-I binds free fatty acids and reduces their intracellular esterification", J. Lipid Res., 2007, pp. 1353-1361, vol. 48.

Eeva-Marjatta Salonen, et al., "Lipoprotein(a) binds to fibronectin and has serine proteinase activity capable of cleaving it", The EMBO Journal, 1989, pp. 4035-4040, vol. 8, No. 13.

Ming-Hui Wei, et al., "In silico-initiated cloning and molecular characterization of a novel human member of the L1 gene family of neural cell adhesion molecules", Hum. Genet., 1998, pp. 355-364, vol. 103.

Fabrizio Briganti, et al., "Carbonic anhydrase catalyzes cyanamide hydration to urea: is it mimicking the physiological reaction?", J. Biol. Inorg. Chem., 1999, pp. 528-536, vol. 4.

Alex Morla, et al., "Superfibronectin is a functionally distinct form of fibronectin", Letters to Nature, Jan. 13, 1994, pp. 193-196, vol. 367.

Leigh Anderson, et al., "Quantitative Mass Spectrometric Multiple Reaction Monitoring Assays for Major Plasma Proteins", Molecular & Cellular Proteomics 5.4, 2006, pp. 573-588, vol. 5.

Leroi V. Desouza, et al., "Absolute Quantification of Potential Cancer Markers in Clinical Tissue Homogenates Using Multiple Reaction Monitoring on a Hybrid Triple Quadrupole/Linear Ion Trap Tandem Mass Spectrometer", Anal. Chem., 2009, pp. 3462-3470, vol. 81.

G. Kohler, et al., "Continuous cultures of fused cells secreting antibody of predefined specificity", Nature, Aug. 7, 1975, pp. 495-497, vol. 256.

Mark H. Zweig, et al., "Receiver-Operating Characteristic (ROC) Plots: A Fundamental Evaluation Tool in Clinical Medicine", Clin. Chem., 1993, pp. 561-577, vol. 39, No. 4.

International Searching Authority, International Search Report for PCT/KR2013/001911 dated Aug. 1, 2013 [PCT/ISA/210].

* cited by examiner

Ratio (cancer/normal) = 1.35
Student T-test : P < 0.001

Ratio (cancer/normal) = 1.43
Student T-test : P < 0.001

Ratio (cancer/normal) = 1.6
Student T-test : P < 0.001

Ratio (cancer/normal) = 1.56
Student T-test : P = 0.005

MULTIPLE BIOMARKER SET FOR BREAST CANCER DIAGNOSIS, METHOD OF DETECTING THE SAME, AND DIAGNOSIS KIT FOR BREAST CANCER USING ANTIBODY AGAINST THE SAME

CROSS REFERENCE TO RELATED APPLICATIONS

This application is a National Stage of International Application No. PCT/KR2013/001911, filed on Mar. 8, 2013, which claims priority from Korean Patent Application No. 10-2012-0023703, filed on Mar. 8, 2012, the contents of all of which are incorporated herein by reference in their entirety.

TECHNICAL FIELD

The present invention relates to a diagnosis of breast cancer. More particularly, the present invention relates to a multiple biomarker set capable of selectively diagnosing an onset of breast cancer in blood, to a method of detecting the same, and to a diagnostic kit for breast cancer comprising an antibody specifically recognizing the same.

BACKGROUND ART

The causes of breast cancer have not been clearly established, but various factors such as female hormones, family history, past medical history, birth history and dietary habits have been considered. According to a survey of the National Statistical Office in 2005, the incidence of breast cancer has been rapidly increasing in these years and overtook the incidence of cervical cancer in 1998. Consequently, while comprising 16.1% of Korean female cancer patients occurred in 2001, the breast cancer surpassed a gastric cancer to hold the first rank. In particular, in 2002, the breast cancer (11.1%) was ranked as a most rapidly increasing cancer in comparison with 2001. In women undergoing physiologically vigorous changes such as a low birth rate, a short feeding period, a early menarche and a late menopause, the incidence of female hormone stimulation has been rapidly increased, thereby increasing a sensitivity of mammary tissue, westernizing the eating habits and polluting a living environment. For these reasons, the incidence of breast cancer is dramatically increased in the recent years.

In view of the actual situation of the current westernization, it is anticipated that increasing the incidence of breast cancer and the mortality due to breast cancer will be kept for a fairly long time in the future. Breast cancer usually results in symptoms such as a lymph node metastasis or an invasion of surrounding tissue due to the growth of cancer cells. However, the majority of the breast cancer can be checked by self-diagnosis without any symptoms. Therefore, in order to reduce the mortality due to breast cancer, it is very important to effectively make an early diagnose of breast cancer (Tuli et al., *Breast J.*, 12: 343-348, 2006).

To diagnose breast cancer, a number of methods have been complexly used. Until now, 70% of breast cancer patients have been hospitalized by the self-diagnosis. However, this self-diagnosis has a disadvantage that it is very difficult to distinguish between malignant tumor and benign tumor lump. In addition, the method for diagnosing breast cancer comprises mammography, ultrasonography, fine-needle aspiration cytology, magnetic resonance radiography and the like, but it is important to check the cancer through biopsy eventually. The mammography refers to a method of taking a breast with X-ray and identifying a breast cancer, and it is excellent in distinguishing whether a tumor lump is benign or malignant. Also, the mammography is a method of finding a latent tumor lump and it is most effective in diagnosing an initial cancer before touching the lump by self-diagnosis. However, the mammography has a disadvantage that a diagnostic yield is decreased in Korean women whose milk line is well-developed like a young women or whose breast is small and fibrous. Further, it is controversy that frequently taking the breast with X-ray may lead to a breast cancer. As an alternative to such mammography, the ultrasonography is used. The ultrasonography is effective in differentiating between a cyst and a hard lump, but the ability to differentiate between malignant tumor and benign tumor lump is decreased.

In order to supplement the disadvantages encountered with such conventional diagnosis methods, there was an attempt to diagnose a breast cancer by measuring a concentration of tumor marker in a blood of patient (Clinton et al., *Biomed Sci. Instrum.* 39: 408-414, 2003; Rui et al., *Proteomics.* 3: 433-439, 2003; Soletormos et al., 48: 229-255, 2001). However, the importance of the diagnostic or prognostic factor of these tumor markers is studied, but its use has still been limited, there being no breast cancer marker officially recommended in the art.

Given the above circumstances, the present inventors have conducted a number of extensive researches in order to develop a method for using, in the diagnosis of breast cancer, a protein marker wherein the protein amount is specifically changed in blood from a breast cancer patient. As a result, the inventors have discovered that comparing the change patterns according to breast cancer of the marker set consisting of a plurality of biomarkers can more effectively diagnose the breast cancer than the method by the change of a single biomarker. In order to effectively track the plurality of protein markers, the inventors have discovered that the breast cancer can be conveniently diagnosed by monitoring the expression level of peptide capable of representing each biomarker protein through a multiple reaction monitoring. The present invention has been completed on the above discovery.

DISCLOSURE

Technical Problem

Accordingly, a purpose of the present invention is to provide a method of conveniently identifying breast cancer using a change pattern according to an onset of breast cancer with a plurality of biomarker set present in blood.

Technical Solution

In order to accomplish the above purpose, the present invention provides a protein marker set for diagnosing breast cancer.

Also, the present invention provides a method for detecting the biomarker set in a blood sample through the multiple reaction monitoring using a triple quadrupole mass spectrometer.

Further, the present invention provides a diagnostic kit for breast cancer comprising antibodies specific to each marker constituting the biomarker set.

In addition, the present invention provides a method for detecting the biomarker set in a blood sample through an antigen-antibody binding reaction using antibodies specific to each marker constituting the biomarker set.

The present invention is, hereinafter, described in more detail.

According to one embodiment, the present invention provides a biomarker set comprising two or more of the five protein markers presented in Table 1 below, for the diagnosis of breast cancer. The biomarker set of the present invention comprises, preferably, three of the below five protein markers, more preferably, four of the below five protein markers, and most preferably, five of the below five protein markers.

TABLE 1

| Recognition | MRM ratio (cancer/normal) | | |
|---|---|---|---|
| number | Breast cancer | Stage I breast cancer | Target protein |
| BM0001 | 0.71 | 0.69 | apolipoprotein C1 |
| BM0002 | 1.35 | 2.01 | apolipoprotein (a) |
| BM0003 | 1.43 | 1.4 | neural cell adhesion molecule L1-like protein |
| BM0004 | 1.6 | 1.61 | carbonic anhydrase 1 |
| BM0005 | 1.56 | 1.54 | fibronectin |
| BM0006 | Internal standard substance | | colon bacillus beta-galactosidase |

The first protein constituting the biomarker set according to the present invention is apolipoprotein C1 set forth in SEQ ID NO: 1. The apolipoprotein C1 binds with a free fatty acid to reduce the esterification thereof in the cells (see Westerterp M. et al., *J. Lipid Res.*, 48:1353-1361, 2007). The second protein is apolipoprotein (a) set forth in SEQ ID NO: 2. The apolipoprotein (a) has an activity of serine proteinase and acts as an autoproteolysis (Salonen E. M. et al., *EMBO J.*, 8: 4035-4040, 1989). The third protein is neural cell adhesion molecule L1-like protein set forth in SEQ ID NO: 3. The neural cell adhesion molecule L1-like protein is a protein which involves in the adhesion of extracellular substrate and cell and plays an important role in a development of nervous system and a synaptic plasticity (Wei M. H. et al., *Hum. Genet.*, 103:355-364, 1998). The fourth protein is carbonic anhydrase 1 set forth in SEQ ID NO: 4. The carbonic anhydrase 1 catalyzes reversible hydration of carbon dioxide and hydration of cyanamide to urea (Briganti F. et al., *J. Biol. Inorg. Chem.*, 4: 528-536, 1999). Finally, the fifth protein is fibronectin set forth in SEQ ID NO: 5. The fibronectin provides a protein adhesion in the adhesion of cell and substrate and conducts a function to migrate the cells into collagen (Morla A. et al., *Nature*, 367: 193-196, 1994).

On the other hand, the multiple reaction monitoring (MRM) using a triple quadrupole mass-spectrometer is an analysis technique wherein certain analytical substances can be selectively separated, detected and quantified to thereby monitor the change of the concentration. MRM is already applied to a quantitative analysis of small molecules, thereby being used in the diagnosis of certain hereditary diseases. MRM method has advantages that it is easy to determine a plurality of peptides simultaneously and that it can identify a relative concentration difference of the protein diagnosis marker candidates between a normal person and a cancer patient without a standard product or an antibody. Further, MRM method has excellent diagnostic sensitivity and selectivity, and it is particularly introduced for the analysis of complex protein and peptide present in blood in the proteomic analysis using a mass spectrometer (Anderson L. et al., *Mol Cell Proteomics*, 5: 375-88, 2006; DeSouza, L. V. et al., *Anal. Chem.*, 81: 3462-70, 2009).

In order to find out a diagnostic protein marker set of which the amount can specifically change in blood from a breast cancer patient to be effectively used in the diagnosis of breast cancer, the present inventors have obtained blood samples from 80 breast cancer patients and 80 non-patient control group, and conducted a quantitative analysis through multiple reaction monitoring (MRM) using a triple quadrupole mass spectrometer. As a result, the present inventors have identified that apolipoprotein C1, apolipoprotein (a), neural cell adhesion molecule L1-like protein, carbonic anhydrase 1 and fibronectin exhibited a change of amount in the blood from the breast cancer patients in comparison with the blood from the non-patient control group and that it is possible to effectively differentiate the breast cancer patients through such change.

When a multiple biomarker set comprising two or more of the five proteins identified in the present invention is used for the diagnosis of breast cancer, it is possible to acquire superior diagnostic accuracy through a mutual complementary action between proteins. Particularly, in the case of a multiple biomarker set comprising five proteins, it is possible to acquire superior diagnostic accuracy incommensurable with a single marker. Further, since the above marker protein set can be detected in the blood, there is no necessity to use the biopsy. Therefore, this can be utilized in the diagnosis of breast cancer in a convenient manner without causing inconvenience to patients.

According to another embodiment, the present invention provides a method for detecting two or more protein markers of apolipoprotein C1, apolipoprotein (a), neural cell adhesion molecule L1-like protein, carbonic anhydrase 1 and fibronectin in a blood sample through a multiple reaction monitoring (MRM) using a triple quadrupole mass spectrometer.

The method of the present invention comprises the steps of:

i) making proteins of a blood sample from a subject and of a blood sample from a control group into peptide fragments;

ii) introducing the above peptide fragments into a triple quadrupole mass spectrometer to conduct a multiple reaction monitoring for two or more of target peptides representing apolipoprotein C1, apolipoprotein (a), neural cell adhesion molecule L1-like protein, carbonic anhydrase 1 and fibronectin, respectively;

iii) representing the results of the multiple reaction monitoring as a percentage to an internal standard substance; and iv) comparing the detection results regarding the subject and the control group.

In accordance with a further embodiment, the onset of breast cancer can be identified by collecting a blood sample from a subject; detecting two or more of the apolipoprotein C1, the apolipoprotein (a), the neural cell adhesion molecule L1-like protein, the carbonic anhydrase 1 and the fibronectin in the blood sample from the subject by MRM method, comparing these detection results with the detection results of a control group and then checking an increase or decrease in the amount of the proteins. Preferably, the onset of breast cancer can be identified by detecting the apolipoprotein C1, the apolipoprotein (a), the neural cell adhesion molecule L1-like protein, the carbonic anhydrase 1 and the fibronectin in a blood sample from a subject by MRM method, comparing the detection results with the detection results of a non-patient control group, and then checking an increase or decrease in the amount of the above five protein markers For the purpose of the present invention, in order to detect the target protein by MRM method, the selection of certain peptide capable of representing each protein and the selection of a pair of mother and daughter ions which is MRM monitoring target of each peptide should be preceded. For the five marker proteins according to the present invention, the target peptide representing apolipoprotein C1 has a sequence of SEQ ID NO: 6 and a pair of mother and daughter ions of the target peptide are m/z 526.8 and m/z 605.3, respectively. The target peptide representing apolipoprotein (a) has a sequence of SEQ ID NO: 7 and a pair of mother and daughter ions of the target peptide are m/z 521.8 and m/z 634.3, respectively. The target peptide representing neural cell adhesion molecule L1-like protein has a sequence of SEQ ID NO: 8 and a pair of mother and daughter ions of the target peptide are m/z 642.8 and m/z 836.4, respectively. The target peptide representing carbonic anhydrase 1 has a sequence of SEQ ID NO: 9 and a pair of mother and daughter of the target peptide are m/z 485.8 and m/z 758.4, respectively. The target peptide representing fibronectin has a sequence of SEQ ID NO: 10 and a pair of mother and daughter of the target peptide are m/z 555.8 and m/z 821.4, respectively.

In addition, in order to detect a target protein, if a certain peptide of which some amino acids are substituted with stable isotopes is synthesized and is used as an internal standard substance upon MRM analysis, the absolute amount of the target protein in the blood can be measured to derive more accurate analysis results. The internal standard substance used in the present invention may comprise any internal standard substance conventionally used in the MRM analysis. For example, colon *bacillus* beta-galactosidase can be used. When a certain peptide of which some amino acids are substituted with stable isotopes is synthesized as the internal standard substance to measure the absolute amount of the target protein in the blood, the amino acids substituted with isotopes comprises, but not limited to, lysine or arginine. As the synthesized peptide, more than 95% pure separated peptide is preferred.

When the biomarker set comprising two or more of the five protein markers of the present invention is detected by MRM method, the sensitivity is excellent as a new diagnostic tool using blood from a patient, and also the selectivity to the protein to be detected is higher than a conventional immunochemical method using antigen-antibody. Further, it is possible to conveniently analyze the blood without using biopsy, and the accuracy to confirm an onset of breast cancer is significantly excellent as compared with the use of a single marker. As such, it can be effectively used for early diagnosis of breast cancer.

In addition, the present invention provides a diagnostic kit for detecting a biomarker set comprising two or more of the five protein markers in a blood sample using the MRM method. The diagnostic kit comprises information regarding a target peptide of each of two or more proteins and a pair of mother and daughter ions of the target peptide, which is needed for detecting two or more protein markers of apolipoprotein C1, apolipoprotein (a), neural cell adhesion molecule L1-like protein, carbonic anhydrase 1 and fibronectin using MRM method. The diagnostic kit further comprises a tool, a reagent and the like generally used for the mass spectrometry in the art. The diagnostic kit comprises, most preferably, information regarding target peptides for all of the five protein markers and pairs of mother and daughter ions of the target peptides.

On the other hand, the biomarker set of the present invention can be detected in a blood sample through antigen-antibody binding reaction as well as through MRM method. Accordingly, in further embodiment, the present invention provides a diagnostic reagent for breast cancer and a diagnostic kit for breast cancer for detecting two or more protein markers in the blood sample comprising two or more of the antibodies specific to each of apolipoprotein C1, apolipoprotein (a), neural cell adhesion molecule L1-like protein, carbonic anhydrase 1 and fibronectin. The diagnostic reagent and kit may comprise, preferably three antibodies, more preferably four antibodies, and most preferably five antibodies, among antibodies specific to each of the five protein markers.

In order to prepare the antibodies selectively binding to each of the protein markers, the above protein markers should be first available. They can be synthesized using amino acid sequences of SEQ ID NO: 1 through SEQ ID NO: 5, or produced from microorganisms using gene recombination, or separated directly from the blood.

For the purpose of the present invention, the above antibody may comprise both polyclonal antibody and monoclonal antibody, but the monoclonal antibody capable of more specifically binding to the antigen is preferred.

The polyclonal antibody can be prepared by injecting a protein marker or a fragment thereof as antigen to an external host in accordance with a conventional method known in the art. Such external host may comprise, for example, mammals such as mouse, rat, sheep and rabbit. The antigen is typically administered by intramuscular, intraperitoneal or subcutaneous injection together with an adjuvant for increasing the antigenicity to thereby immunize the external host Serum is regularly collected from the immunized external host. Subsequently, the serum showing increased potency and specificity to the antigen can be acquired, or the antibody can be separated and purified therefrom, thereby preparing a polyclonal antibody specific to the marker protein.

The monoclonal antibody can be prepared by a process for producing an immortalized cell line by fusion known in the art (Kohler G. et al., *Nature*, 256: 495-497, 1975). Briefly explaining the above process, a mouse is first immunized by a pure marker protein or a fragment thereof. Or the mouse is immunized by synthesizing the peptide thereof and coupling it to a bovine serum albumin. The antibody-producing B lymphocytes separated from the immunized mouse are fused with myeloma cells of human or mouse to produce immortalized hybridoma cells. Subsequently, the generation of a monoclonal antibody in the hybridoma cells is investigated by an enzyme-linked immunosorbent assay (ELISA) to select a positive clone. The selected clone is cultured and then an antibody is separated and purified. Or the clone can be injected into an abdominal cavity of a rat to collect ascites, thereby preparing a monoclonal antibody specific to the marker protein.

The antibody used in the detection of the protein marker of the present invention comprises a complete form having two full-length light chains and two full-length heavy chains as well as a functional fragment of an antibody molecule. The functional fragment of the antibody molecule refers to a fragment having at least antigen binding capacity. Examples thereof include Fab, F(ab'), F(ab')$_2$, Fv and the like.

The diagnostic kit for breast cancer according to the present invention comprises antibodies selectively recognizing each of the five protein markers as well as a tool and reagent generally used for an immunologic analysis in the art.

In accordance with one embodiment of the present invention, the diagnostic kit for breast cancer may comprise two or more of the five antibodies specific to each of the five protein markers; a secondary antibody conjugate to which a marker colored by a reaction with a substrate is conjugated; a coloring substrate solution which is subject to the color development reaction with the marker; a washing solution; and an enzyme reaction stopping solution.

The diagnostic kit for breast cancer according to the present invention may further comprise a positive control group containing the five marker protein standard antigens and a negative control group containing anti-serum from an animal to which the antigen is not introduced.

The diagnostic kit for breast cancer according to the present invention can diagnose breast cancer by quantitatively or qualitatively analyzing an antigen to the antibody protein through an antigen-antibody binding reaction. The antigen-antibody binding reaction may be determined by using conventional enzyme-linked immunosorbent assay (ELISA), radioimmunoassay (RIA), sandwich assay, western blotting, immunoprecipitation, immunohistochemical staining, fluorescence immunoassay, enzyme substrate coloring method, antigen-antibody aggregation and the like. For example, the diagnostic kit is provided so as to conduct ELISA which reacts with a recombinant monoclonal antibody protein using 96-well microtiter plate wherein the subject and the control are coated on the surface.

A fixed body for the antigen-antibody binding reaction used herein may include nitrocellulose membrane, PVDF membrane, well plate synthesized with polyvinyl resin or polystyrene resin, slide glass made of glass and the like.

The marker of the secondary antibody is preferably a conventional coloring agent conducting a coloring reaction. The marker used herein may comprise fluorescein and dye including horseradish peroxidase (HRP), alkaline phosphatase, colloid gold, poly L-lysine-fluorescein isothiocyanate (FITC) or rhodamine-B-isothiocyanate (RITC).

It is preferable to use the coloring substrate for inducing color development depending on the marker conducting a coloring reaction. For example, the coloring substrate used herein is selected from the group consisting of 3,3',5,5'-tetramethyl benzidine (TMB), 2,2'-azino-bis(3-ethylbenzothiazoline-6-sulfonic acid (ABTS), o-phenylenediamine (OPD) and the like. The coloring substrate is preferably provided in a state dissolved in a buffer solution (0.1 M NaAc, pH 5.5). The coloring substrate such as TMB is decomposed by HRP used as a marker of the secondary antibody conjugate to produce a color developed deposition body. The presence or absence of the marker protein can be detected by visually checking the deposition level of the developed deposition body.

The washing solution comprises, preferably, a phosphate buffer solution, NaCl and Tween 20. The buffer solution (PBST) consisting of 0.02 M phosphate buffer solution, 0.13 M NaCl and 0.05% Tween 20 is more preferred. After antigen-antibody binding reaction, the secondary antibody is reacted with the antigen-antibody conjugate. An appropriate amount of the washing solution is then added to a fixed body and washed 3 to 6 times. The reaction stopping solution used herein may comprise, preferably, sulfuric acid solution ($H_2SO_4$).

In addition, a further aspect of the present invention provides a method of detecting two or more of the protein markers of apolipoprotein C1, apolipoprotein (a), neural cell adhesion molecule L1-like protein, carbonic anhydrase 1, and fibronectin in a blood sample through an antigen-antibody binding reaction using the antibodies specific to each protein marker. Preferably, the present invention provides a method for detecting three protein markers in a blood sample through an antigen-antibody binding reaction using the antibodies specific to each of the five proteins. More preferably, the present invention provides a method for detecting four protein markers. Most preferably, the present invention provides a method for detecting the five protein markers.

The above detection method comprises fixing a protein in blood or separating a protein with electrophoresis (SDS-PAGE), transferring the protein to PVDF membrane, contacting the same with an antibody selectively recognizing the protein of the above protein marker group to thereby indirectly check the presence of the marker protein group through an antigen-antibody binding reaction. The antigen-antibody binding reaction may include enzyme-linked immunosorbent assay (ELISA), radioimmunoassay (RIA), sandwich assay, western blotting, immunoprecipitation, immunohistochemical staining, fluorescence immunoassay, enzyme substrate coloring method, antigen-antibody aggregation and the like. The sample used herein may comprise serum, plasma or blood. The plasma is most preferred.

According to a preferred embodiment of the present invention, the above detection method may comprise the steps of:

i) coating or fixing proteins of a blood sample from a subject and of a blood sample from a control group to a fixed body;

ii) adding to the above fixed body two or more of the antibodies specific to each protein of apolipoprotein C1, apolipoprotein (a), neural cell adhesion molecule L1-like protein, carbonic anhydrase 1 and fibronectin to conduct an antigen-antibody bonding reaction;

iii) detecting the antigen-antibody boding reaction product produced through the antigen-antibody bonding reaction using a secondary antibody conjugate and a coloring substrate solution; and iv) comparing the detection results concerning the blood sample from the subject and the blood sample from the control group.

One embodiment of the above detection method comprises first separating plasma proteins from a blood sample depending on the molecular weight thereof by electrophoresis, transferring and fixing the separated proteins to a fixed body such as PVDF membrane. The antigen-antibody binding reaction is then conducted by adding to the fixed protein antigen an antibody specific to each marker protein. If the marker protein is present in the blood sample, the antigen-antibody binding reaction occurs when the antibody specific to the marker protein is added to the fixed membrane. In order to determine the binding level of the marker protein and the antibody thereto, the step of binding a secondary antibody having an affinity to the marker protein antibody, for example, anti-human IgG-HRP is conducted. Whether horseradish peroxidase (HRP) conjugated to the secondary antibody is reacted with enhanced chemiluminescence (ECL) substrate to develop color, and the degree of the color development are compared with those of the control group. Consequently, the presence or absence of the protein marker for diagnosing breast cancer in the blood sample and the increase or decrease of the amount thereof as compared with the control group are detected.

On the other hand, in the case of using a biological microchip and an automated microarray system wherein two or more of the antibodies specific to each of the five protein markers of the present invention are fixed on a biological microchip and then reacted with a blood sample separated from a subject to detect an antigen to the antibody protein, it is advantageous that a large number of samples can be analyzed by a single analysis. Accordingly, the present invention provides a biochip wherein two or more of the antibodies specifically binding to each of the five protein markers of the present invention are integrated on a solid substrate. The solid substrate of the biochip used herein may comprise, for example, plastic, glass, metal, silicone, etc.

Advantageous Effects

As described above, the method for detecting a biomarker set comprising two or more of the five protein markers of the present invention in a blood sample through MRM method has advantages that the sensitivity is excellent as a new diagnostic tool using blood from a patient, and the selectivity to the protein to be detected is higher than a conventional immunochemical method using antigen-antibody. Further, it is possible to conveniently analyze the blood without using biopsy. Since the kit and method for diagnosing breast cancer using the antibodies to the biomarker set use as a sample blood which can be relatively easy to collect, the breast cancer can be very conveniently diagnosed without imposing a burden on the patient, differently from a conventional method for diagnosing breast cancer which is subject to biopsy. Additionally, the accuracy and sensitivity in the diagnosis of breast cancer is high. The method for detecting such biomarker set by MRM method or antigen-antibody reaction can provide very high accuracy and sensitivity in comparison with the diagnosis method using a single marker. As such, it can be effectively used for early diagnosis of breast cancer.

BEST MODE

Figure 1A:
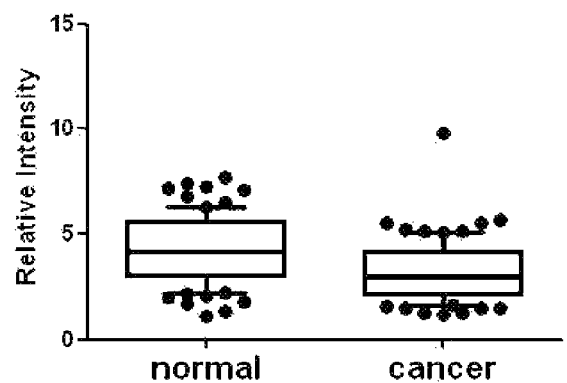
FIGS. 1a and 1b are a diagram showing a concentration of antigen (ratio to colon *bacillus* beta-galactosidase) in which apolipoprotein C1 marker protein was measured from 80 breast cancer patients and 80 non-patients (control group) by MRM method:
 a: Box diagram; and
 b: ROC curve.

The present invention is further illustrated by the following examples, which are not to be construed to limit the scope of the invention.

EXAMPLE 1

Detection of Biomarker Set for Diagnosing Breast Cancer Using a Multiple Reaction Monitoring (MRM)

In order to check whether the protein group shown in Table 1 above can be used as a marker for selectively diagnosing breast cancer in blood, the present inventors have utilized a method for quantitative analysis through a multiple reaction monitoring (MRM) using a triple quadrupole mass spectrometer as follows (Anderson L. et al., *Mol Cell Proteomics*, 5: 375-88, 2006). MRM refers to a method mainly used in the quantitative analysis using a mass spectrometer, which obtains information by observing a certain daughter ion produced from mother ion in interest. For example, if only one ion of several mother ions with m/z 1000 has daughter ion with m/z 500, it is MRM that the mother ion with m/z 1000 is selected and fragmented and then daughter ion with m/z 500 is inspected to trace such ion.

1.1 Preparation of Sample

In order to identify the efficiency of the five biomarker proteins according to the present invention, the expression levels of the proteins in the blood samples from 80 breast cancer patients and 80 non-patients were compared to confirm the diagnostic efficiency of breast cancer of the biomarker set by a statistical processing. 200 μg of protein samples were prepared from the blood obtained from 160 people, respectively. Each prepared sample was treated with 10 mM of dithiothreitol and reacted for one hour, thereby breaking coupling between thiol residues of cystines of amino acids in the protein which may interfere with the process for making a protein into a peptide fragment. Such broken thiol coupling was treated with 60 mM of iodoacetamide and reacted for one hour in a place without light to prevent re-coupling between thiol residues. To the prepared protein sample, 4 μg of trypsin 20 μl (Promega, USA) which is an amount corresponding to 1/50 of the entire protein 200 μg, was added and then treated at 37° C. for 16 hours to separate into a plurality of peptide fragments. The peptide fragments thus obtained were prepared as final samples for mass spectrometry by removing a salt using C18 cartridge.

1.2 Multiple Reaction Monitoring Using a Triple Quadrupole Mass Spectrometer

In order to conduct MRM analysis, a peptide capable of representing a specific protein should be selected, and a daughter ion produced through fragmentation from the peptide, i.e., a pair of mother and daughter ions capable of effectively monitoring the target peptide should be selected. In order to select a pair of mother and daughter ions of the five proteins presented in Table 1, the blood samples were subject to tandem mass spectrometry to thereby identify apolipoprotein C1 and apolipoprotein (a). From the tandem mass spectrometry spectrum, the peptide of SEQ ID NO: 6 capable of representing apolipoprotein C1, and the peptide of SEQ ID NO: 7 capable of representing apolipoprotein (a) were selected, and also a pair of mother and daughter ions of these peptides was selected, and shown in Tale 2 below.

In order to indentify the retention time in column of the other three proteins which could not check from the direct tandem mass spectrometry of the blood samples, and the tandem mass spectrometry spectrum thereof, the peptides capable of representing the other three proteins (neural cell adhesion molecule L1-like protein, carbonic anhydrase 1 and fibronectin), respectively, were synthesized (JPT Peptide Technologies Gmbh, Germany). As a result, the neural cell adhesion molecule L1-like protein selected was the peptide set forth in SEQ ID NO: 8; the carbonic anhydrase 1 selected was the peptide set forth in SEQ ID NO: 9; and the fibronectin selected was the peptide set forth in SEQ ID NO: 10. A pair of mother and daughter ions of these peptides was selected. The results are shown in Table 2 below.

TABLE 2

| Marker | Target peptide | MRM transition (m/z) | |
|---|---|---|---|
| | | Mother ion | Daughter ion |
| apolipoprotein C1 | EFGNTLEDK | 526.8 | 605.3 |
| apolipoprotein (a) | GTYSTTVTGR | 521.8 | 634.3 |
| neural cell adhesion molecule L1-like protein | GDLYFANVEEK | 642.8 | 836.4 |
| carbonic anhydrase 1 | VLDALQAIK | 485.8 | 758.4 |
| Fibronectin | STTPDITGYR | 555.8 | 821.4 |
| colon *bacillus* beta-galactosidase | GDFQFNISR | 542.3 | 636.3 |

The final samples prepared in Example 1.1 were subject to reversed phase resin chromatograph to separate the plasma peptide fragments. Consequently, MRM spectra of each peptide were obtained using a triple quadrupole mass spectrometer (apparatus: 5500 Qtrap, AB Sciex, USA). The reversed phase resin chromatograph was conducted with HALO™ C18 column (Eksigent, USA) using 5%~40% acetonitrile concentration gradient for 45 minutes. The peak area of the MRM chromatogram of the target peptide was calculated by MultiQuant™ computer quantitative analysis program (AB Sciex, USA). The quantitative value of each target peptide was represented as a percentage to the peak area of colon *bacillus* beta-galactosidase (Table 2) introduced as an internal standard substance. The difference of protein expression levels between breast cancer patients and a non-patient control group can be identified by obtaining the MRM chromatogram area ratio of each peptide.

Figure 1B:
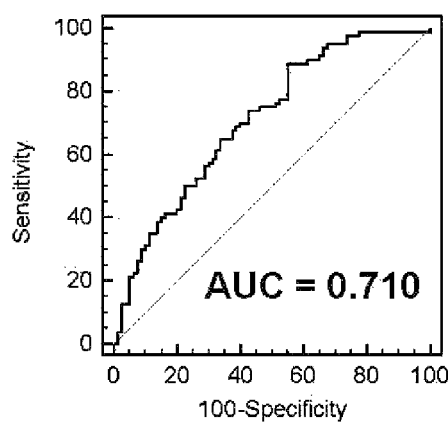

The concentrations of each of the five marker proteins measured by the above method were shown in graphs. Specifically, in the case of apolipoprotein C1 set forth in SEQ ID NO: 1, the results shown in the box diagram as in FIG. 1a demonstrated that the breast cancer patients exhibited a 1.41 times reduction in the above marker protein in comparison with the non-patient control group. Also, the results shown in the receptor-operating characteristics (ROC) curve as in FIG. 1b demonstrated that the area under the curve (AUC) of the above marker protein was 0.71.

Figure 2A:
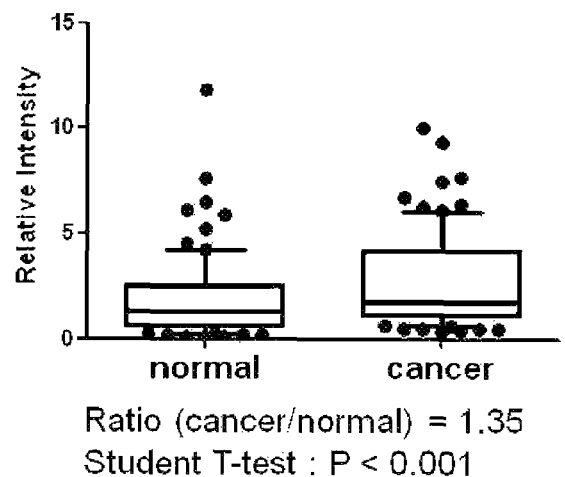
FIGS. 2a and 2b are a diagram showing a concentration of antigen (ratio to colon *bacillus* beta-galactosidase) in which apolipoprotein (a) marker protein was measured from 80 breast cancer patients and 80 non-patients (control group) by MRM method:
 a: Box diagram; and
 b: ROC curve.
Figure 2B:
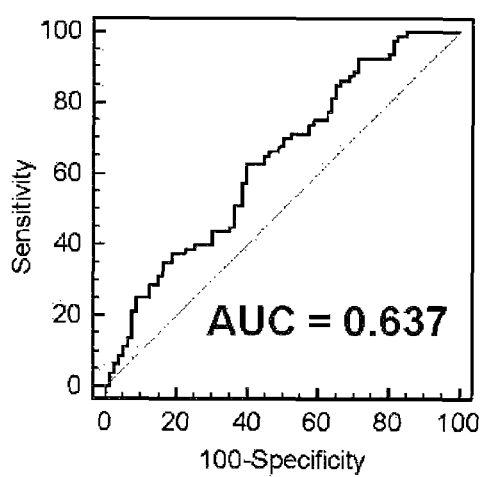

In the case of apolipoprotein (a) set forth in SEQ ID NO: 2, the results shown in the box diagram as in FIG. 2a demonstrated that the breast cancer patients exhibited a 1.35 times increase in the above marker protein in comparison with the non-patient control group. Also, the results shown in the receptor-operating characteristics (ROC) curve as in FIG. 2b demonstrated that the area under the curve (AUC) of the above marker protein was 0.64.

Figure 3A:
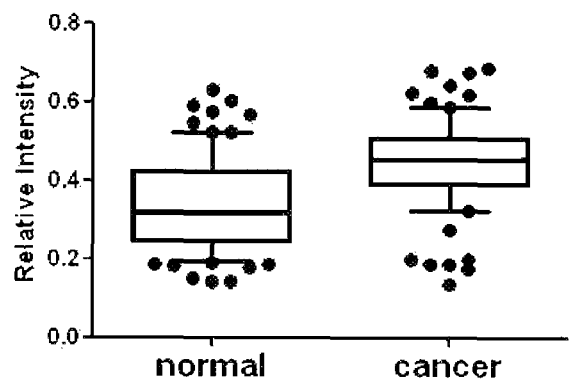
FIGS. 3a and 3b are a diagram showing a concentration of antigen (ratio to colon *bacillus* beta-galactosidase) in which neural cell adhesion molecule L1-like protein was measured from 80 breast cancer patients and 80 non-patients (control group) by MRM method:
 a: Box diagram; and
 b: ROC curve.
Figure 3B:
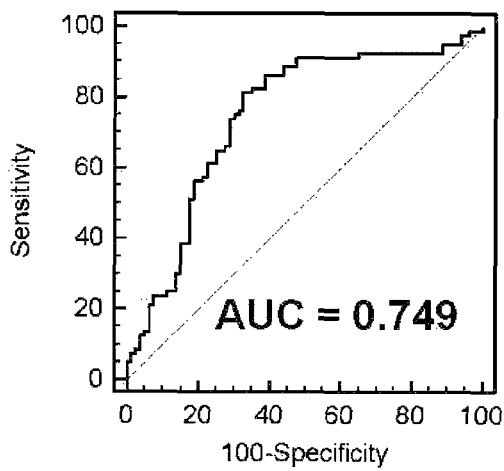

In the case of neural cell adhesion molecule L1-like protein set forth in SEQ ID NO: 3, the results shown in the box diagram as in FIG. 3a demonstrated that the breast cancer patients exhibited a 1.43 times increase in the above marker protein in comparison with the non-patient control group. Also, the results shown in the receptor-operating characteristics (ROC) curve as in FIG. 3b demonstrated that the area under the curve (AUC) of the above marker protein was 0.75.

Figure 4A:
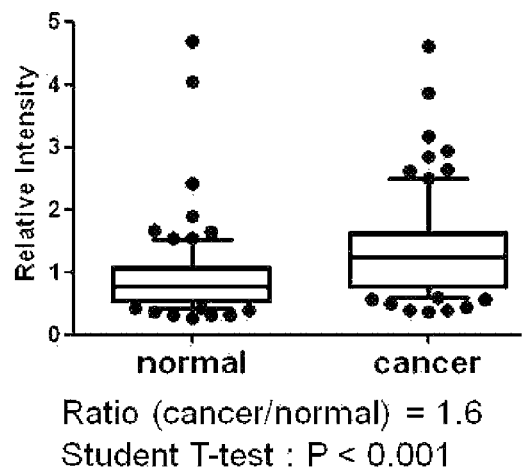
FIGS. 4a and 4b are a diagram showing a concentration of antigen (ratio to colon *bacillus* beta-galactosidase) in which carbonic anhydrase 1 marker protein was measured from 80 breast cancer patients and 80 non-patients (control group) by MRM method:
 a: Box diagram; and
 b: ROC curve.
Figure 4B:
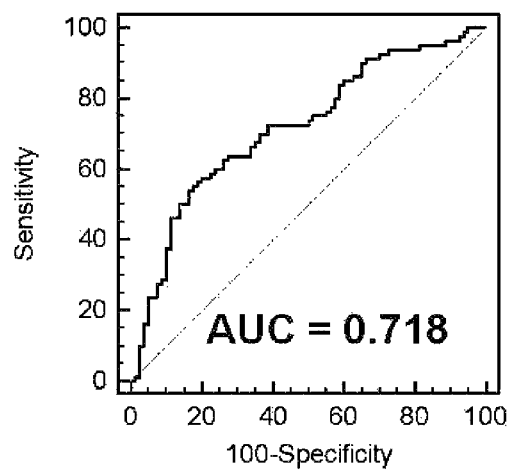

In the case of carbonic anhydrase 1 set forth in SEQ ID NO: 4, the results shown in the box diagram as in FIG. 4a demonstrated that the breast cancer patients exhibited a 1.60 times increase in the above marker protein in comparison with the non-patient control group. Also, the results shown in the receptor-operating characteristics (ROC) curve as in FIG. 4b demonstrated that the area under the curve (AUC) of the above marker protein was 0.72.

Figure 5A:
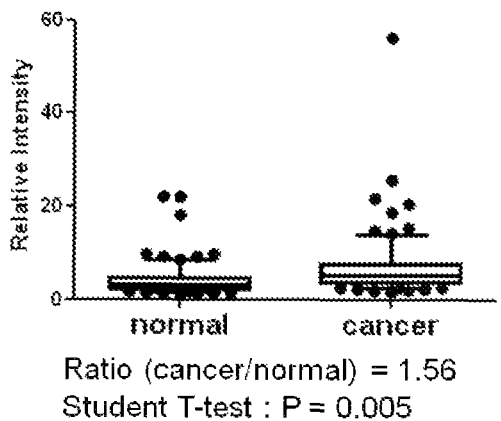
FIGS. 5a and 5b are a diagram showing a concentration of antigen (ratio to colon *bacillus* beta-galactosidase) in which fibronectin marker protein was measured from 80 breast cancer patients and 80 non-patients (control group) by MRM method:
 a: Box diagram; and
 b: ROC curve.
Figure 5B:
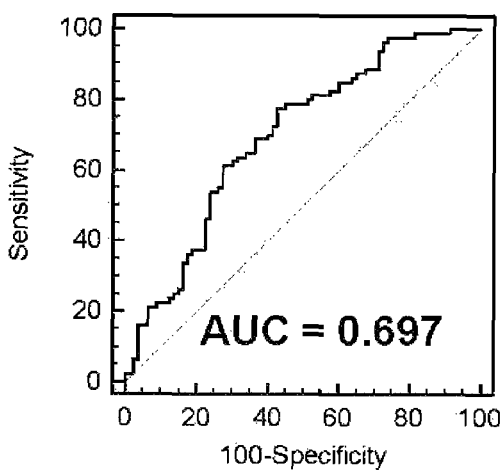

Finally, in the case of fibronectin set forth in SEQ ID NO: 5, the results shown in the box diagram as in FIG. 5a demonstrated that the breast cancer patients exhibited a 1.56 times increase in the above marker protein in comparison with the non-patient control group. Also, the results shown in the receptor-operating characteristics (ROC) curve as in FIG. 5b demonstrated that the area under the curve (AUC) of the above marker protein was 0.70.

For reference, the ROC curve is a graph of all susceptibility/specificity pairs obtained by consecutively changing determination titer over the entire range of observed data and it mainly shows the accuracy of the test (Zweig et al., *Clin. Chem.* 39:561-577,1993).

1.3 Diagnosis of Breast Cancer Through Biomarker Set

The quantitative results of the five marker protein group identified in Example 1.2 were unified through logistic regression and one diagnostic marker consisting of a plurality of markers (multi labeling markers) was prepared to confirm the diagnostic efficiency of breast cancer.

Figure 6A:
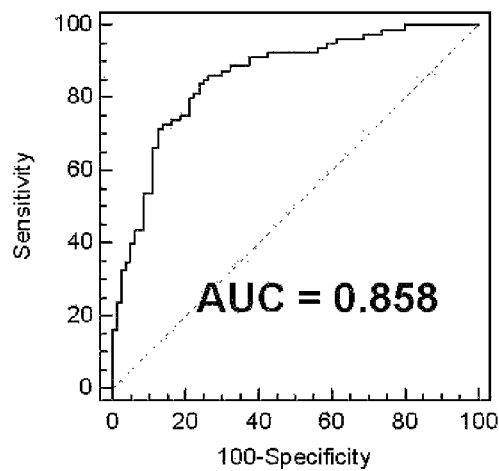
FIGS. 6a is a diagram showing, as ROC curve, a concentration of antigen (ratio to colon *bacillus* beta-galactosidase) in which the biomarker set presented in Table 1 was measured from 80 breast cancer patients and 80 non-patients (control group) by MRM method.

As a result, the results shown in the receptor-operating characteristic (ROC) curve for 80 breast cancer patients and 80 non-patient control group as in FIG. 6a demonstrated that the area under the curve (AUC) of the multiple labeling markers was 0.86. The results showed a sensitivity of 75% at a specificity of 80%. As such, it could be seen that the above analysis has higher sensitivity and accuracy than a conventional single labeling marker.

Figure 6B:
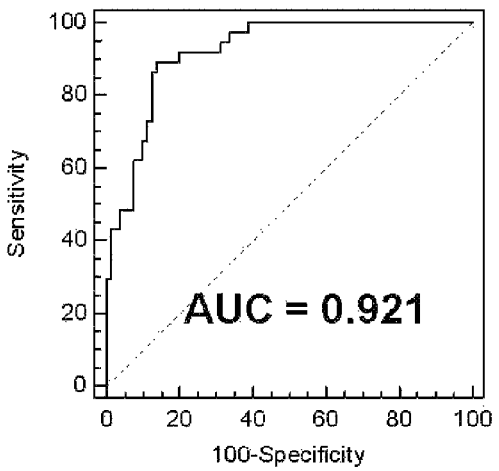
FIG. 6b is a diagram showing, as ROC curve, a concentration of antigen (ratio to colon *bacillus* beta-galactosidase) in which the biomarker set presented in Table 1 was measured from 37 stage I breast cancer patients and 80 non-patients (control group) by MRM method.

In addition, the results of the receptor-operating characteristic (ROC) curve for 80 non-patients and 37 stage I breast cancer patients as in FIG. 6b demonstrated that the area under the curve (AUC) of the multiple labeling markers was 0.92. Also, the results showed a sensitivity of 92% at a specificity of 80%. As such, it could be seen that the above analysis is very effective in diagnosing initial breast cancer.

We claim:

1. A method for detecting a biomarker set in a blood sample through multiple reaction monitoring using a triple quadrupole mass spectrometer, wherein the method comprises the steps of:
   i) obtaining a blood sample from a subject with initial breast cancer and digesting the proteins from the blood sample into peptide fragments;
   ii) introducing the above peptide fragments into the triple quadrupole mass spectrometer to conduct multiple reaction monitoring for target peptides representing the biomarker set;
   iii) representing the results of the multiple reaction monitoring as a percentage to an internal standard substance;
   wherein the biomarker set consists of apolipoprotein C1 set forth in SEQ ID NO: 1, apolipoprotein (a) set forth in SEQ ID NO: 2, neural cell adhesion molecule L1-like protein set forth in SEQ ID NO: 3, carbonic anhydrase 1 set forth in SEQ ID NO: 4, and fibronectin set forth in SEQ ID NO: 5; and
   wherein the target peptide of the apolipoprotein C1 has the sequence of SEQ ID NO: 6 and the pair of mother and daughter ions of the target peptide are m/z 526.8 and m/z 605.3, respectively; the target peptide of the apolipoprotein (a) has the sequence of SEQ ID NO: 7 and the pair of mother and daughter ions of the target peptide is m/z 521.8 and m/z 634.3, respectively; the target peptide of the neural cell adhesion molecule L1-like protein has the sequence of SEQ ID NO: 8 and the pair of mother and daughter ions of the target peptide are m/z 642.8 and m/z 836.4, respectively; the target peptide of the carbonic anhydrase 1 has the sequence of SEQ ID NO: 9 and the pair of mother and daughter ions of the target peptide are m/z 485.8 and m/z 758,4, respectively; and the target peptide of the fibronectin has the sequence of SEQ ID NO: 10 and the pair of mother and daughter ions of the target peptide are m/z 555.8 and m/z 821.4, respectively.

2. The method of claim 1, wherein colon *bacillus* beta-galactosidase is used as an internal standard substance and the target peptide representing colon bacillus beta-galactosidase has a sequence of SEQ ID NO: 11 and a pair of mother and daughter ions are m/z 542.3 and m/z 636.3, respectively.

3. The method of claim 1, wherein the blood sample is plasma or serum.

* * * * *

SEQUENCE LISTING

<160> NUMBER OF SEQ ID NOS: 11

<210> SEQ ID NO 1
<211> LENGTH: 83
<212> TYPE: PRT
<213> ORGANISM: Homo sapiens

<400> SEQUENCE: 1

```
Met Arg Leu Phe Leu Ser Leu Pro Val Leu Val Val Leu Ser Ile
 1               5                  10                  15

Val Leu Glu Gly Pro Ala Pro Ala Gln Gly Thr Pro Asp Val Ser Ser
             20                  25                  30

Ala Leu Asp Lys Leu Lys Glu Phe Gly Asn Thr Leu Glu Asp Lys Ala
         35                  40                  45

Arg Glu Leu Ile Ser Arg Ile Lys Gln Ser Glu Leu Ser Ala Lys Met
     50                  55                  60

Arg Glu Trp Phe Ser Glu Thr Phe Gln Lys Val Lys Glu Lys Leu Lys
 65                  70                  75                  80

Ile Asp Ser
```

<210> SEQ ID NO 2
<211> LENGTH: 4548
<212> TYPE: PRT
<213> ORGANISM: Homo sapiens

<400> SEQUENCE: 2

```
Met Glu His Lys Glu Val Val Leu Leu Leu Leu Phe Leu Lys Ser
 1               5                  10                  15

Ala Ala Pro Glu Gln Ser His Val Val Gln Asp Cys Tyr His Gly Asp
             20                  25                  30

Gly Gln Ser Tyr Arg Gly Thr Tyr Ser Thr Thr Val Thr Gly Arg Thr
         35                  40                  45

Cys Gln Ala Trp Ser Ser Met Thr Pro His Gln His Asn Arg Thr Thr
     50                  55                  60

Glu Asn Tyr Pro Asn Ala Gly Leu Ile Met Asn Tyr Cys Arg Asn Pro
 65                  70                  75                  80

Asp Ala Val Ala Ala Pro Tyr Cys Tyr Thr Arg Asp Pro Gly Val Arg
             85                  90                  95

Trp Glu Tyr Cys Asn Leu Thr Gln Cys Ser Asp Ala Glu Gly Thr Ala
        100                 105                 110

Val Ala Pro Pro Thr Val Thr Pro Val Pro Ser Leu Glu Ala Pro Ser
        115                 120                 125

Glu Gln Ala Pro Thr Glu Gln Arg Pro Gly Val Gln Glu Cys Tyr His
    130                 135                 140

Gly Asn Gly Gln Ser Tyr Arg Gly Thr Tyr Ser Thr Thr Val Thr Gly
145                 150                 155                 160

Arg Thr Cys Gln Ala Trp Ser Ser Met Thr Pro His Ser His Ser Arg
                165                 170                 175

Thr Pro Glu Tyr Tyr Pro Asn Ala Gly Leu Ile Met Asn Tyr Cys Arg
            180                 185                 190

Asn Pro Asp Ala Val Ala Ala Pro Tyr Cys Tyr Thr Arg Asp Pro Gly
        195                 200                 205

Val Arg Trp Glu Tyr Cys Asn Leu Thr Gln Cys Ser Asp Ala Glu Gly
    210                 215                 220

Thr Ala Val Ala Pro Pro Thr Val Thr Pro Val Pro Ser Leu Glu Ala
225                 230                 235                 240
```

```
Pro Ser Glu Gln Ala Pro Thr Glu Gln Arg Pro Gly Val Gln Glu Cys
            245                 250                 255

Tyr His Gly Asn Gly Gln Ser Tyr Arg Gly Thr Tyr Ser Thr Thr Val
            260                 265                 270

Thr Gly Arg Thr Cys Gln Ala Trp Ser Ser Met Thr Pro His Ser His
            275                 280                 285

Ser Arg Thr Pro Glu Tyr Tyr Pro Asn Ala Gly Leu Ile Met Asn Tyr
            290                 295                 300

Cys Arg Asn Pro Asp Ala Val Ala Ala Pro Tyr Cys Tyr Thr Arg Asp
305                 310                 315                 320

Pro Gly Val Arg Trp Glu Tyr Cys Asn Leu Thr Gln Cys Ser Asp Ala
                325                 330                 335

Glu Gly Thr Ala Val Ala Pro Pro Thr Val Thr Pro Val Pro Ser Leu
            340                 345                 350

Glu Ala Pro Ser Glu Gln Ala Pro Thr Glu Gln Arg Pro Gly Val Gln
            355                 360                 365

Glu Cys Tyr His Gly Asn Gly Gln Ser Tyr Arg Gly Thr Tyr Ser Thr
            370                 375                 380

Thr Val Thr Gly Arg Thr Cys Gln Ala Trp Ser Ser Met Thr Pro His
385                 390                 395                 400

Ser His Ser Arg Thr Pro Glu Tyr Tyr Pro Asn Ala Gly Leu Ile Met
                405                 410                 415

Asn Tyr Cys Arg Asn Pro Asp Ala Val Ala Ala Pro Tyr Cys Tyr Thr
            420                 425                 430

Arg Asp Pro Gly Val Arg Trp Glu Tyr Cys Asn Leu Thr Gln Cys Ser
            435                 440                 445

Asp Ala Glu Gly Thr Ala Val Ala Pro Pro Thr Val Thr Pro Val Pro
450                 455                 460

Ser Leu Glu Ala Pro Ser Glu Gln Ala Pro Thr Glu Gln Arg Pro Gly
465                 470                 475                 480

Val Gln Glu Cys Tyr His Gly Asn Gly Gln Ser Tyr Arg Gly Thr Tyr
                485                 490                 495

Ser Thr Thr Val Thr Gly Arg Thr Cys Gln Ala Trp Ser Ser Met Thr
            500                 505                 510

Pro His Ser His Ser Arg Thr Pro Glu Tyr Tyr Pro Asn Ala Gly Leu
            515                 520                 525

Ile Met Asn Tyr Cys Arg Asn Pro Asp Ala Val Ala Ala Pro Tyr Cys
530                 535                 540

Tyr Thr Arg Asp Pro Gly Val Arg Trp Glu Tyr Cys Asn Leu Thr Gln
545                 550                 555                 560

Cys Ser Asp Ala Glu Gly Thr Ala Val Ala Pro Pro Thr Val Thr Pro
                565                 570                 575

Val Pro Ser Leu Glu Ala Pro Ser Glu Gln Ala Pro Thr Glu Gln Arg
            580                 585                 590

Pro Gly Val Gln Glu Cys Tyr His Gly Asn Gly Gln Ser Tyr Arg Gly
            595                 600                 605

Thr Tyr Ser Thr Thr Val Thr Gly Arg Thr Cys Gln Ala Trp Ser Ser
            610                 615                 620

Met Thr Pro His Ser His Ser Arg Thr Pro Glu Tyr Tyr Pro Asn Ala
625                 630                 635                 640

Gly Leu Ile Met Asn Tyr Cys Arg Asn Pro Asp Ala Val Ala Ala Pro
                645                 650                 655
```

-continued

Tyr Cys Tyr Thr Arg Asp Pro Gly Val Arg Trp Glu Tyr Cys Asn Leu
            660                 665                 670

Thr Gln Cys Ser Asp Ala Glu Gly Thr Ala Val Ala Pro Pro Thr Val
675                 680                 685

Thr Pro Val Pro Ser Leu Glu Ala Pro Ser Glu Gln Ala Pro Thr Glu
        690                 695                 700

Gln Arg Pro Gly Val Gln Glu Cys Tyr His Gly Asn Gly Gln Ser Tyr
705                 710                 715                 720

Arg Gly Thr Tyr Ser Thr Thr Val Thr Gly Arg Thr Cys Gln Ala Trp
                725                 730                 735

Ser Ser Met Thr Pro His Ser His Ser Arg Thr Pro Glu Tyr Tyr Pro
            740                 745                 750

Asn Ala Gly Leu Ile Met Asn Tyr Cys Arg Asn Pro Asp Ala Val Ala
            755                 760                 765

Ala Pro Tyr Cys Tyr Thr Arg Asp Pro Gly Val Arg Trp Glu Tyr Cys
        770                 775                 780

Asn Leu Thr Gln Cys Ser Asp Ala Glu Gly Thr Ala Val Ala Pro Pro
785                 790                 795                 800

Thr Val Thr Pro Val Pro Ser Leu Glu Ala Pro Ser Glu Gln Ala Pro
                805                 810                 815

Thr Glu Gln Arg Pro Gly Val Gln Glu Cys Tyr His Gly Asn Gly Gln
            820                 825                 830

Ser Tyr Arg Gly Thr Tyr Ser Thr Thr Val Thr Gly Arg Thr Cys Gln
                835                 840                 845

Ala Trp Ser Ser Met Thr Pro His Ser His Ser Arg Thr Pro Glu Tyr
850                 855                 860

Tyr Pro Asn Ala Gly Leu Ile Met Asn Tyr Cys Arg Asn Pro Asp Ala
865                 870                 875                 880

Val Ala Ala Pro Tyr Cys Tyr Thr Arg Asp Pro Gly Val Arg Trp Glu
                885                 890                 895

Tyr Cys Asn Leu Thr Gln Cys Ser Asp Ala Glu Gly Thr Ala Val Ala
            900                 905                 910

Pro Pro Thr Val Thr Pro Val Pro Ser Leu Glu Ala Pro Ser Glu Gln
        915                 920                 925

Ala Pro Thr Glu Gln Arg Pro Gly Val Gln Glu Cys Tyr His Gly Asn
    930                 935                 940

Gly Gln Ser Tyr Arg Gly Thr Tyr Ser Thr Thr Val Thr Gly Arg Thr
945                 950                 955                 960

Cys Gln Ala Trp Ser Ser Met Thr Pro His Ser His Ser Arg Thr Pro
                965                 970                 975

Glu Tyr Tyr Pro Asn Ala Gly Leu Ile Met Asn Tyr Cys Arg Asn Pro
            980                 985                 990

Asp Ala Val Ala Ala Pro Tyr Cys Tyr Thr Arg Asp Pro Gly Val Arg
        995                 1000                1005

Trp Glu Tyr Cys Asn Leu Thr Gln Cys Ser Asp Ala Glu Gly Thr Ala
    1010                1015                1020

Val Ala Pro Pro Thr Val Thr Pro Val Pro Ser Leu Glu Ala Pro Ser
1025                1030                1035                1040

Glu Gln Ala Pro Thr Glu Gln Arg Pro Gly Val Gln Glu Cys Tyr His
                1045                1050                1055

Gly Asn Gly Gln Ser Tyr Arg Gly Thr Tyr Ser Thr Thr Val Thr Gly
            1060                1065                1070

Arg Thr Cys Gln Ala Trp Ser Ser Met Thr Pro His Ser His Ser Arg

-continued

```
           1075                1080                1085
Thr Pro Glu Tyr Tyr Pro Asn Ala Gly Leu Ile Met Asn Tyr Cys Arg
       1090                1095                1100
Asn Pro Asp Ala Val Ala Ala Pro Tyr Cys Tyr Thr Arg Asp Pro Gly
1105                1110                1115                1120
Val Arg Trp Glu Tyr Cys Asn Leu Thr Gln Cys Ser Asp Ala Glu Gly
               1125                1130                1135
Thr Ala Val Ala Pro Pro Thr Val Thr Pro Val Pro Ser Leu Glu Ala
           1140                1145                1150
Pro Ser Glu Gln Ala Pro Thr Glu Gln Arg Pro Gly Val Gln Glu Cys
       1155                1160                1165
Tyr His Gly Asn Gly Gln Ser Tyr Arg Gly Thr Tyr Ser Thr Thr Val
   1170                1175                1180
Thr Gly Arg Thr Cys Gln Ala Trp Ser Ser Met Thr Pro His Ser His
1185                1190                1195                1200
Ser Arg Thr Pro Glu Tyr Tyr Pro Asn Ala Gly Leu Ile Met Asn Tyr
               1205                1210                1215
Cys Arg Asn Pro Asp Ala Val Ala Ala Pro Tyr Cys Tyr Thr Arg Asp
           1220                1225                1230
Pro Gly Val Arg Trp Glu Tyr Cys Asn Leu Thr Gln Cys Ser Asp Ala
       1235                1240                1245
Glu Gly Thr Ala Val Ala Pro Pro Thr Val Thr Pro Val Pro Ser Leu
   1250                1255                1260
Glu Ala Pro Ser Glu Gln Ala Pro Thr Glu Gln Arg Pro Gly Val Gln
1265                1270                1275                1280
Glu Cys Tyr His Gly Asn Gly Gln Ser Tyr Arg Gly Thr Tyr Ser Thr
               1285                1290                1295
Thr Val Thr Gly Arg Thr Cys Gln Ala Trp Ser Ser Met Thr Pro His
           1300                1305                1310
Ser His Ser Arg Thr Pro Glu Tyr Tyr Pro Asn Ala Gly Leu Ile Met
       1315                1320                1325
Asn Tyr Cys Arg Asn Pro Asp Ala Val Ala Ala Pro Tyr Cys Tyr Thr
   1330                1335                1340
Arg Asp Pro Gly Val Arg Trp Glu Tyr Cys Asn Leu Thr Gln Cys Ser
1345                1350                1355                1360
Asp Ala Glu Gly Thr Ala Val Ala Pro Pro Thr Val Thr Pro Val Pro
               1365                1370                1375
Ser Leu Glu Ala Pro Ser Glu Gln Ala Pro Thr Glu Gln Arg Pro Gly
           1380                1385                1390
Val Gln Glu Cys Tyr His Gly Asn Gly Gln Ser Tyr Arg Gly Thr Tyr
       1395                1400                1405
Ser Thr Thr Val Thr Gly Arg Thr Cys Gln Ala Trp Ser Ser Met Thr
   1410                1415                1420
Pro His Ser His Ser Arg Thr Pro Glu Tyr Tyr Pro Asn Ala Gly Leu
1425                1430                1435                1440
Ile Met Asn Tyr Cys Arg Asn Pro Asp Ala Val Ala Ala Pro Tyr Cys
               1445                1450                1455
Tyr Thr Arg Asp Pro Gly Val Arg Trp Glu Tyr Cys Asn Leu Thr Gln
           1460                1465                1470
Cys Ser Asp Ala Glu Gly Thr Ala Val Ala Pro Pro Thr Val Thr Pro
       1475                1480                1485
Val Pro Ser Leu Glu Ala Pro Ser Glu Gln Ala Pro Thr Glu Gln Arg
   1490                1495                1500
```

```
Pro Gly Val Gln Glu Cys Tyr His Gly Asn Gly Gln Ser Tyr Arg Gly
1505                1510                1515                1520

Thr Tyr Ser Thr Thr Val Thr Gly Arg Thr Cys Gln Ala Trp Ser Ser
            1525                1530                1535

Met Thr Pro His Ser His Ser Arg Thr Pro Glu Tyr Tyr Pro Asn Ala
            1540                1545                1550

Gly Leu Ile Met Asn Tyr Cys Arg Asn Pro Asp Ala Val Ala Ala Pro
            1555                1560                1565

Tyr Cys Tyr Thr Arg Asp Pro Gly Val Arg Trp Glu Tyr Cys Asn Leu
        1570                1575                1580

Thr Gln Cys Ser Asp Ala Glu Gly Thr Ala Val Ala Pro Pro Thr Val
1585                1590                1595                1600

Thr Pro Val Pro Ser Leu Glu Ala Pro Ser Glu Gln Ala Pro Thr Glu
            1605                1610                1615

Gln Arg Pro Gly Val Gln Glu Cys Tyr His Gly Asn Gly Gln Ser Tyr
            1620                1625                1630

Arg Gly Thr Tyr Ser Thr Thr Val Thr Gly Arg Thr Cys Gln Ala Trp
        1635                1640                1645

Ser Ser Met Thr Pro His Ser His Ser Arg Thr Pro Glu Tyr Tyr Pro
    1650                1655                1660

Asn Ala Gly Leu Ile Met Asn Tyr Cys Arg Asn Pro Asp Ala Val Ala
1665                1670                1675                1680

Ala Pro Tyr Cys Tyr Thr Arg Asp Pro Gly Val Arg Trp Glu Tyr Cys
            1685                1690                1695

Asn Leu Thr Gln Cys Ser Asp Ala Glu Gly Thr Ala Val Ala Pro Pro
        1700                1705                1710

Thr Val Thr Pro Val Pro Ser Leu Glu Ala Pro Ser Glu Gln Ala Pro
    1715                1720                1725

Thr Glu Gln Arg Pro Gly Val Gln Glu Cys Tyr His Gly Asn Gly Gln
1730                1735                1740

Ser Tyr Arg Gly Thr Tyr Ser Thr Thr Val Thr Gly Arg Thr Cys Gln
1745                1750                1755                1760

Ala Trp Ser Ser Met Thr Pro His Ser His Ser Arg Thr Pro Glu Tyr
            1765                1770                1775

Tyr Pro Asn Ala Gly Leu Ile Met Asn Tyr Cys Arg Asn Pro Asp Ala
            1780                1785                1790

Val Ala Ala Pro Tyr Cys Tyr Thr Arg Asp Pro Gly Val Arg Trp Glu
        1795                1800                1805

Tyr Cys Asn Leu Thr Gln Cys Ser Asp Ala Glu Gly Thr Ala Val Ala
    1810                1815                1820

Pro Pro Thr Val Thr Pro Val Pro Ser Leu Glu Ala Pro Ser Glu Gln
1825                1830                1835                1840

Ala Pro Thr Glu Gln Arg Pro Gly Val Gln Glu Cys Tyr His Gly Asn
            1845                1850                1855

Gly Gln Ser Tyr Arg Gly Thr Tyr Ser Thr Thr Val Thr Gly Arg Thr
            1860                1865                1870

Cys Gln Ala Trp Ser Ser Met Thr Pro His Ser His Ser Arg Thr Pro
        1875                1880                1885

Glu Tyr Tyr Pro Asn Ala Gly Leu Ile Met Asn Tyr Cys Arg Asn Pro
    1890                1895                1900

Asp Ala Val Ala Ala Pro Tyr Cys Tyr Thr Arg Asp Pro Gly Val Arg
1905                1910                1915                1920
```

Trp Glu Tyr Cys Asn Leu Thr Gln Cys Ser Asp Ala Glu Gly Thr Ala
            1925                1930                1935

Val Ala Pro Pro Thr Val Thr Pro Val Pro Ser Leu Glu Ala Pro Ser
        1940                1945                1950

Glu Gln Ala Pro Thr Glu Gln Arg Pro Gly Val Gln Glu Cys Tyr His
        1955                1960                1965

Gly Asn Gly Gln Ser Tyr Arg Gly Thr Tyr Ser Thr Thr Val Thr Gly
    1970                1975                1980

Arg Thr Cys Gln Ala Trp Ser Ser Met Thr Pro His Ser His Ser Arg
1985                1990                1995                2000

Thr Pro Glu Tyr Tyr Pro Asn Ala Gly Leu Ile Met Asn Tyr Cys Arg
            2005                2010                2015

Asn Pro Asp Ala Val Ala Ala Pro Tyr Cys Tyr Thr Arg Asp Pro Gly
        2020                2025                2030

Val Arg Trp Glu Tyr Cys Asn Leu Thr Gln Cys Ser Asp Ala Glu Gly
            2035                2040                2045

Thr Ala Val Ala Pro Pro Thr Val Thr Pro Val Pro Ser Leu Glu Ala
        2050                2055                2060

Pro Ser Glu Gln Ala Pro Thr Glu Gln Arg Pro Gly Val Gln Glu Cys
2065                2070                2075                2080

Tyr His Gly Asn Gly Gln Ser Tyr Arg Gly Thr Tyr Ser Thr Thr Val
            2085                2090                2095

Thr Gly Arg Thr Cys Gln Ala Trp Ser Ser Met Thr Pro His Ser His
        2100                2105                2110

Ser Arg Thr Pro Glu Tyr Tyr Pro Asn Ala Gly Leu Ile Met Asn Tyr
        2115                2120                2125

Cys Arg Asn Pro Asp Ala Val Ala Ala Pro Tyr Cys Tyr Thr Arg Asp
2130                2135                2140

Pro Gly Val Arg Trp Glu Tyr Cys Asn Leu Thr Gln Cys Ser Asp Ala
2145                2150                2155                2160

Glu Gly Thr Ala Val Ala Pro Pro Thr Val Thr Pro Val Pro Ser Leu
            2165                2170                2175

Glu Ala Pro Ser Glu Gln Ala Pro Thr Glu Gln Arg Pro Gly Val Gln
        2180                2185                2190

Glu Cys Tyr His Gly Asn Gly Gln Ser Tyr Arg Gly Thr Tyr Ser Thr
        2195                2200                2205

Thr Val Thr Gly Arg Thr Cys Gln Ala Trp Ser Ser Met Thr Pro His
    2210                2215                2220

Ser His Ser Arg Thr Pro Glu Tyr Tyr Pro Asn Ala Gly Leu Ile Met
2225                2230                2235                2240

Asn Tyr Cys Arg Asn Pro Asp Ala Val Ala Ala Pro Tyr Cys Tyr Thr
            2245                2250                2255

Arg Asp Pro Gly Val Arg Trp Glu Tyr Cys Asn Leu Thr Gln Cys Ser
        2260                2265                2270

Asp Ala Glu Gly Thr Ala Val Ala Pro Pro Thr Val Thr Pro Val Pro
    2275                2280                2285

Ser Leu Glu Ala Pro Ser Glu Gln Ala Pro Thr Glu Gln Arg Pro Gly
    2290                2295                2300

Val Gln Glu Cys Tyr His Gly Asn Gly Gln Ser Tyr Arg Gly Thr Tyr
2305                2310                2315                2320

Ser Thr Thr Val Thr Gly Arg Thr Cys Gln Ala Trp Ser Ser Met Thr
            2325                2330                2335

Pro His Ser His Ser Arg Thr Pro Glu Tyr Tyr Pro Asn Ala Gly Leu

-continued

```
            2340              2345              2350
Ile Met Asn Tyr Cys Arg Asn Pro Asp Ala Val Ala Ala Pro Tyr Cys
        2355              2360              2365

Tyr Thr Arg Asp Pro Gly Val Arg Trp Glu Tyr Cys Asn Leu Thr Gln
        2370              2375              2380

Cys Ser Asp Ala Glu Gly Thr Ala Val Ala Pro Pro Thr Val Thr Pro
2385              2390              2395              2400

Val Pro Ser Leu Glu Ala Pro Ser Gln Ala Pro Thr Glu Gln Arg
            2405              2410              2415

Pro Gly Val Gln Glu Cys Tyr His Gly Asn Gly Gln Ser Tyr Arg Gly
            2420              2425              2430

Thr Tyr Ser Thr Thr Val Thr Gly Arg Thr Cys Gln Ala Trp Ser Ser
        2435              2440              2445

Met Thr Pro His Ser His Ser Arg Thr Pro Glu Tyr Tyr Pro Asn Ala
        2450              2455              2460

Gly Leu Ile Met Asn Tyr Cys Arg Asn Pro Asp Ala Val Ala Ala Pro
2465              2470              2475              2480

Tyr Cys Tyr Thr Arg Asp Pro Gly Val Arg Trp Glu Tyr Cys Asn Leu
            2485              2490              2495

Thr Gln Cys Ser Asp Ala Glu Gly Thr Ala Val Ala Pro Pro Thr Val
            2500              2505              2510

Thr Pro Val Pro Ser Leu Glu Ala Pro Ser Gln Ala Pro Thr Glu
        2515              2520              2525

Gln Arg Pro Gly Val Gln Glu Cys Tyr His Gly Asn Gly Gln Ser Tyr
        2530              2535              2540

Arg Gly Thr Tyr Ser Thr Thr Val Thr Gly Arg Thr Cys Gln Ala Trp
2545              2550              2555              2560

Ser Ser Met Thr Pro His Ser His Ser Arg Thr Pro Glu Tyr Tyr Pro
            2565              2570              2575

Asn Ala Gly Leu Ile Met Asn Tyr Cys Arg Asn Pro Asp Ala Val Ala
            2580              2585              2590

Ala Pro Tyr Cys Tyr Thr Arg Asp Pro Gly Val Arg Trp Glu Tyr Cys
        2595              2600              2605

Asn Leu Thr Gln Cys Ser Asp Ala Glu Gly Thr Ala Val Ala Pro Pro
2610              2615              2620

Thr Val Thr Pro Val Pro Ser Leu Glu Ala Pro Ser Gln Ala Pro
2625              2630              2635              2640

Thr Glu Gln Arg Pro Gly Val Gln Glu Cys Tyr His Gly Asn Gly Gln
            2645              2650              2655

Ser Tyr Arg Gly Thr Tyr Ser Thr Thr Val Thr Gly Arg Thr Cys Gln
            2660              2665              2670

Ala Trp Ser Ser Met Thr Pro His Ser His Ser Arg Thr Pro Glu Tyr
        2675              2680              2685

Tyr Pro Asn Ala Gly Leu Ile Met Asn Tyr Cys Arg Asn Pro Asp Ala
        2690              2695              2700

Val Ala Ala Pro Tyr Cys Tyr Thr Arg Asp Pro Gly Val Arg Trp Glu
2705              2710              2715              2720

Tyr Cys Asn Leu Thr Gln Cys Ser Asp Ala Glu Gly Thr Ala Val Ala
            2725              2730              2735

Pro Pro Thr Val Thr Pro Val Pro Ser Leu Glu Ala Pro Ser Glu Gln
            2740              2745              2750

Ala Pro Thr Glu Gln Arg Pro Gly Val Gln Glu Cys Tyr His Gly Asn
        2755              2760              2765
```

```
Gly Gln Ser Tyr Arg Gly Thr Tyr Ser Thr Thr Val Thr Gly Arg Thr
         2770            2775            2780

Cys Gln Ala Trp Ser Ser Met Thr Pro His Ser His Ser Arg Thr Pro
2785            2790            2795            2800

Glu Tyr Tyr Pro Asn Ala Gly Leu Ile Met Asn Tyr Cys Arg Asn Pro
             2805            2810            2815

Asp Ala Val Ala Ala Pro Tyr Cys Tyr Thr Arg Asp Pro Gly Val Arg
         2820            2825            2830

Trp Glu Tyr Cys Asn Leu Thr Gln Cys Ser Asp Ala Glu Gly Thr Ala
         2835            2840            2845

Val Ala Pro Pro Thr Val Thr Pro Val Pro Ser Leu Glu Ala Pro Ser
         2850            2855            2860

Glu Gln Ala Pro Thr Glu Gln Arg Pro Gly Val Gln Glu Cys Tyr His
2865            2870            2875            2880

Gly Asn Gly Gln Ser Tyr Arg Gly Thr Tyr Ser Thr Thr Val Thr Gly
                 2885            2890            2895

Arg Thr Cys Gln Ala Trp Ser Ser Met Thr Pro His Ser His Ser Arg
         2900            2905            2910

Thr Pro Glu Tyr Tyr Pro Asn Ala Gly Leu Ile Met Asn Tyr Cys Arg
         2915            2920            2925

Asn Pro Asp Ala Val Ala Ala Pro Tyr Cys Tyr Thr Arg Asp Pro Gly
         2930            2935            2940

Val Arg Trp Glu Tyr Cys Asn Leu Thr Gln Cys Ser Asp Ala Glu Gly
2945            2950            2955            2960

Thr Ala Val Ala Pro Pro Thr Val Thr Pro Val Pro Ser Leu Glu Ala
             2965            2970            2975

Pro Ser Glu Gln Ala Pro Thr Glu Gln Arg Pro Gly Val Gln Glu Cys
             2980            2985            2990

Tyr His Gly Asn Gly Gln Ser Tyr Arg Gly Thr Tyr Ser Thr Thr Val
         2995            3000            3005

Thr Gly Arg Thr Cys Gln Ala Trp Ser Ser Met Thr Pro His Ser His
3010            3015            3020

Ser Arg Thr Pro Glu Tyr Tyr Pro Asn Ala Gly Leu Ile Met Asn Tyr
3025            3030            3035            3040

Cys Arg Asn Pro Asp Ala Val Ala Ala Pro Tyr Cys Tyr Thr Arg Asp
             3045            3050            3055

Pro Gly Val Arg Trp Glu Tyr Cys Asn Leu Thr Gln Cys Ser Asp Ala
             3060            3065            3070

Glu Gly Thr Ala Val Ala Pro Pro Thr Val Thr Pro Val Pro Ser Leu
             3075            3080            3085

Glu Ala Pro Ser Glu Gln Ala Pro Thr Glu Gln Arg Pro Gly Val Gln
         3090            3095            3100

Glu Cys Tyr His Gly Asn Gly Gln Ser Tyr Arg Gly Thr Tyr Ser Thr
3105            3110            3115            3120

Thr Val Thr Gly Arg Thr Cys Gln Ala Trp Ser Ser Met Thr Pro His
                 3125            3130            3135

Ser His Ser Arg Thr Pro Glu Tyr Tyr Pro Asn Ala Gly Leu Ile Met
             3140            3145            3150

Asn Tyr Cys Arg Asn Pro Asp Ala Val Ala Ala Pro Tyr Cys Tyr Thr
         3155            3160            3165

Arg Asp Pro Gly Val Arg Trp Glu Tyr Cys Asn Leu Thr Gln Cys Ser
         3170            3175            3180
```

-continued

```
Asp Ala Glu Gly Thr Ala Val Ala Pro Pro Thr Val Thr Pro Val Pro
3185                3190                3195                3200

Ser Leu Glu Ala Pro Ser Glu Gln Ala Pro Thr Glu Gln Arg Pro Gly
            3205                3210                3215

Val Gln Glu Cys Tyr His Gly Asn Gly Gln Ser Tyr Arg Gly Thr Tyr
        3220                3225                3230

Ser Thr Thr Val Thr Gly Arg Thr Cys Gln Ala Trp Ser Ser Met Thr
    3235                3240                3245

Pro His Ser His Ser Arg Thr Pro Glu Tyr Tyr Pro Asn Ala Gly Leu
3250                3255                3260

Ile Met Asn Tyr Cys Arg Asn Pro Asp Ala Val Ala Ala Pro Tyr Cys
3265                3270                3275                3280

Tyr Thr Arg Asp Pro Gly Val Arg Trp Glu Tyr Cys Asn Leu Thr Gln
            3285                3290                3295

Cys Ser Asp Ala Glu Gly Thr Ala Val Ala Pro Pro Thr Val Thr Pro
        3300                3305                3310

Val Pro Ser Leu Glu Ala Pro Ser Glu Gln Ala Pro Thr Glu Gln Arg
    3315                3320                3325

Pro Gly Val Gln Glu Cys Tyr His Gly Asn Gly Gln Ser Tyr Arg Gly
3330                3335                3340

Thr Tyr Ser Thr Thr Val Thr Gly Arg Thr Cys Gln Ala Trp Ser Ser
3345                3350                3355                3360

Met Thr Pro His Ser His Ser Arg Thr Pro Glu Tyr Tyr Pro Asn Ala
            3365                3370                3375

Gly Leu Ile Met Asn Tyr Cys Arg Asn Pro Asp Pro Val Ala Ala Pro
        3380                3385                3390

Tyr Cys Tyr Thr Arg Asp Pro Ser Val Arg Trp Glu Tyr Cys Asn Leu
    3395                3400                3405

Thr Gln Cys Ser Asp Ala Glu Gly Thr Ala Val Ala Pro Pro Thr Ile
3410                3415                3420

Thr Pro Ile Pro Ser Leu Glu Ala Pro Ser Glu Gln Ala Pro Thr Glu
3425                3430                3435                3440

Gln Arg Pro Gly Val Gln Glu Cys Tyr His Gly Asn Gly Gln Ser Tyr
            3445                3450                3455

Gln Gly Thr Tyr Phe Ile Thr Val Thr Gly Arg Thr Cys Gln Ala Trp
        3460                3465                3470

Ser Ser Met Thr Pro His Ser His Ser Arg Thr Pro Ala Tyr Tyr Pro
    3475                3480                3485

Asn Ala Gly Leu Ile Lys Asn Tyr Cys Arg Asn Pro Asp Pro Val Ala
3490                3495                3500

Ala Pro Trp Cys Tyr Thr Thr Asp Pro Ser Val Arg Trp Glu Tyr Cys
3505                3510                3515                3520

Asn Leu Thr Arg Cys Ser Asp Ala Glu Trp Thr Ala Phe Val Pro Pro
            3525                3530                3535

Asn Val Ile Leu Ala Pro Ser Leu Glu Ala Phe Phe Glu Gln Ala Leu
        3540                3545                3550

Thr Glu Glu Thr Pro Gly Val Gln Asp Cys Tyr Tyr His Tyr Gly Gln
    3555                3560                3565

Ser Tyr Arg Gly Thr Tyr Ser Thr Thr Val Thr Gly Arg Thr Cys Gln
3570                3575                3580

Ala Trp Ser Ser Met Thr Pro His Gln His Ser Arg Thr Pro Glu Asn
3585                3590                3595                3600

Tyr Pro Asn Ala Gly Leu Thr Arg Asn Tyr Cys Arg Asn Pro Asp Ala
```

```
            3605                3610                3615

Glu Ile Arg Pro Trp Cys Tyr Thr Met Asp Pro Ser Val Arg Trp Glu
        3620                3625                3630

Tyr Cys Asn Leu Thr Gln Cys Leu Val Thr Glu Ser Ser Val Leu Ala
        3635                3640            3645

Thr Leu Thr Val Val Pro Asp Pro Ser Thr Glu Ala Ser Ser Glu Glu
    3650                3655                3660

Ala Pro Thr Glu Gln Ser Pro Gly Val Gln Asp Cys Tyr His Gly Asp
3665                3670                3675                3680

Gly Gln Ser Tyr Arg Gly Ser Phe Ser Thr Thr Val Thr Gly Arg Thr
        3685                3690                3695

Cys Gln Ser Trp Ser Ser Met Thr Pro His Trp His Gln Arg Thr Thr
        3700                3705                3710

Glu Tyr Tyr Pro Asn Gly Gly Leu Thr Arg Asn Tyr Cys Arg Asn Pro
    3715                3720                3725

Asp Ala Glu Ile Ser Pro Trp Cys Tyr Thr Met Asp Pro Asn Val Arg
    3730                3735            3740

Trp Glu Tyr Cys Asn Leu Thr Gln Cys Pro Val Thr Glu Ser Ser Val
3745                3750                3755                3760

Leu Ala Thr Ser Thr Ala Val Ser Glu Gln Ala Pro Thr Glu Gln Ser
        3765                3770                3775

Pro Thr Val Gln Asp Cys Tyr His Gly Asp Gly Gln Ser Tyr Arg Gly
        3780                3785                3790

Ser Phe Ser Thr Thr Val Thr Gly Arg Thr Cys Gln Ser Trp Ser Ser
    3795                3800                3805

Met Thr Pro His Trp His Gln Arg Thr Thr Glu Tyr Tyr Pro Asn Gly
    3810                3815                3820

Gly Leu Thr Arg Asn Tyr Cys Arg Asn Pro Asp Ala Glu Ile Arg Pro
3825                3830                3835                3840

Trp Cys Tyr Thr Met Asp Pro Ser Val Arg Trp Glu Tyr Cys Asn Leu
        3845                3850                3855

Thr Gln Cys Pro Val Met Glu Ser Thr Leu Leu Thr Thr Pro Thr Val
        3860                3865                3870

Val Pro Val Pro Ser Thr Glu Leu Pro Ser Glu Glu Ala Pro Thr Glu
    3875                3880                3885

Asn Ser Thr Gly Val Gln Asp Cys Tyr Arg Gly Asp Gly Gln Ser Tyr
    3890                3895                3900

Arg Gly Thr Leu Ser Thr Thr Ile Thr Gly Arg Thr Cys Gln Ser Trp
3905                3910                3915                3920

Ser Ser Met Thr Pro His Trp His Arg Arg Ile Pro Leu Tyr Tyr Pro
        3925                3930                3935

Asn Ala Gly Leu Thr Arg Asn Tyr Cys Arg Asn Pro Asp Ala Glu Ile
        3940                3945                3950

Arg Pro Trp Cys Tyr Thr Met Asp Pro Ser Val Arg Trp Glu Tyr Cys
    3955                3960                3965

Asn Leu Thr Arg Cys Pro Val Thr Glu Ser Ser Val Leu Thr Thr Pro
    3970                3975                3980

Thr Val Ala Pro Val Pro Ser Thr Glu Ala Pro Ser Glu Gln Ala Pro
3985                3990                3995                4000

Pro Glu Lys Ser Pro Val Val Gln Asp Cys Tyr His Gly Asp Gly Arg
        4005                4010                4015

Ser Tyr Arg Gly Ile Ser Ser Thr Thr Val Thr Gly Arg Thr Cys Gln
        4020                4025                4030
```

```
Ser Trp Ser Ser Met Ile Pro His Trp His Gln Arg Thr Pro Glu Asn
        4035                4040                4045

Tyr Pro Asn Ala Gly Leu Thr Glu Asn Tyr Cys Arg Asn Pro Asp Ser
    4050                4055                4060

Gly Lys Gln Pro Trp Cys Tyr Thr Thr Asp Pro Cys Val Arg Trp Glu
4065                4070                4075                4080

Tyr Cys Asn Leu Thr Gln Cys Ser Glu Thr Glu Ser Gly Val Leu Glu
            4085                4090                4095

Thr Pro Thr Val Val Pro Val Pro Ser Met Glu Ala His Ser Glu Ala
        4100                4105                4110

Ala Pro Thr Glu Gln Thr Pro Val Val Arg Gln Cys Tyr His Gly Asn
    4115                4120                4125

Gly Gln Ser Tyr Arg Gly Thr Phe Ser Thr Thr Val Thr Gly Arg Thr
    4130                4135                4140

Cys Gln Ser Trp Ser Ser Met Thr Pro His Arg His Gln Arg Thr Pro
4145                4150                4155                4160

Glu Asn Tyr Pro Asn Asp Gly Leu Thr Met Asn Tyr Cys Arg Asn Pro
            4165                4170                4175

Asp Ala Asp Thr Gly Pro Trp Cys Phe Thr Met Asp Pro Ser Ile Arg
            4180                4185                4190

Trp Glu Tyr Cys Asn Leu Thr Arg Cys Ser Asp Thr Glu Gly Thr Val
        4195                4200                4205

Val Ala Pro Pro Thr Val Ile Gln Val Pro Ser Leu Gly Pro Pro Ser
    4210                4215                4220

Glu Gln Asp Cys Met Phe Gly Asn Gly Lys Gly Tyr Arg Gly Lys Lys
4225                4230                4235                4240

Ala Thr Thr Val Thr Gly Thr Pro Cys Gln Glu Trp Ala Ala Gln Glu
        4245                4250                4255

Pro His Arg His Ser Thr Phe Ile Pro Gly Thr Asn Lys Trp Ala Gly
        4260                4265                4270

Leu Glu Lys Asn Tyr Cys Arg Asn Pro Asp Gly Asp Ile Asn Gly Pro
            4275                4280                4285

Trp Cys Tyr Thr Met Asn Pro Arg Lys Leu Phe Asp Tyr Cys Asp Ile
    4290                4295                4300

Pro Leu Cys Ala Ser Ser Ser Phe Asp Cys Gly Lys Pro Gln Val Glu
4305                4310                4315                4320

Pro Lys Lys Cys Pro Gly Ser Ile Val Gly Gly Cys Val Ala His Pro
            4325                4330                4335

His Ser Trp Pro Trp Gln Val Ser Leu Arg Thr Arg Phe Gly Lys His
        4340                4345                4350

Phe Cys Gly Gly Thr Leu Ile Ser Pro Glu Trp Val Leu Thr Ala Ala
    4355                4360                4365

His Cys Leu Lys Lys Ser Ser Arg Pro Ser Ser Tyr Lys Val Ile Leu
    4370                4375                4380

Gly Ala His Gln Glu Val Asn Leu Glu Ser His Val Gln Glu Ile Glu
4385                4390                4395                4400

Val Ser Arg Leu Phe Leu Glu Pro Thr Gln Ala Asp Ile Ala Leu Leu
        4405                4410                4415

Lys Leu Ser Arg Pro Ala Val Ile Thr Asp Lys Val Met Pro Ala Cys
        4420                4425                4430

Leu Pro Ser Pro Asp Tyr Met Val Thr Ala Arg Thr Glu Cys Tyr Ile
        4435                4440                4445
```

-continued

```
Thr Gly Trp Gly Glu Thr Gln Gly Thr Phe Gly Thr Gly Leu Leu Lys
    4450                4455                4460

Glu Ala Gln Leu Leu Val Ile Glu Asn Glu Val Cys Asn His Tyr Lys
4465                4470                4475                4480

Tyr Ile Cys Ala Glu His Leu Ala Arg Gly Thr Asp Ser Cys Gln Gly
                4485                4490                4495

Asp Ser Gly Gly Pro Leu Val Cys Phe Glu Lys Asp Lys Tyr Ile Leu
                4500                4505                4510

Gln Gly Val Thr Ser Trp Gly Leu Gly Cys Ala Arg Pro Asn Lys Pro
                4515                4520                4525

Gly Val Tyr Ala Arg Val Ser Arg Phe Val Thr Trp Ile Glu Gly Met
            4530                4535                4540

Met Arg Asn Asn
4545

<210> SEQ ID NO 3
<211> LENGTH: 1208
<212> TYPE: PRT
<213> ORGANISM: Homo sapiens

<400> SEQUENCE: 3

Met Glu Pro Leu Leu Leu Gly Arg Gly Leu Ile Val Tyr Leu Met Phe
  1               5                  10                  15

Leu Leu Leu Lys Phe Ser Lys Ala Ile Glu Ile Pro Ser Ser Val Gln
                20                  25                  30

Gln Val Pro Thr Ile Ile Lys Gln Ser Lys Val Gln Val Ala Phe Pro
            35                  40                  45

Phe Asp Glu Tyr Phe Gln Ile Glu Cys Glu Ala Lys Gly Asn Pro Glu
 50                  55                  60

Pro Thr Phe Ser Trp Thr Lys Asp Gly Asn Pro Phe Tyr Phe Thr Asp
 65                  70                  75                  80

His Arg Ile Ile Pro Ser Asn Asn Ser Gly Thr Phe Arg Ile Pro Asn
                85                  90                  95

Glu Gly His Ile Ser His Phe Gln Gly Lys Tyr Arg Cys Phe Ala Ser
            100                 105                 110

Asn Lys Leu Gly Ile Ala Met Ser Glu Glu Ile Glu Phe Ile Val Pro
        115                 120                 125

Ser Val Pro Lys Phe Pro Lys Glu Lys Ile Asp Pro Leu Glu Val Glu
        130                 135                 140

Glu Gly Asp Pro Ile Val Leu Pro Cys Asn Pro Pro Lys Gly Leu Pro
145                 150                 155                 160

Pro Leu His Ile Tyr Trp Met Asn Ile Glu Leu Glu His Ile Glu Gln
                165                 170                 175

Asp Glu Arg Val Tyr Met Ser Gln Lys Gly Asp Leu Tyr Phe Ala Asn
            180                 185                 190

Val Glu Glu Lys Asp Ser Arg Asn Asp Tyr Cys Cys Phe Ala Ala Phe
        195                 200                 205

Pro Arg Leu Arg Thr Ile Val Gln Lys Met Pro Met Lys Leu Thr Val
    210                 215                 220

Asn Ser Ser Asn Ser Ile Lys Gln Arg Lys Pro Lys Leu Leu Leu Pro
225                 230                 235                 240

Pro Thr Glu Ser Gly Ser Glu Ser Ser Ile Thr Ile Leu Lys Gly Glu
                245                 250                 255

Ile Leu Leu Leu Glu Cys Phe Ala Glu Gly Leu Pro Thr Pro Gln Val
            260                 265                 270
```

```
Asp Trp Asn Lys Ile Gly Gly Asp Leu Pro Lys Gly Arg Glu Thr Lys
        275                 280                 285

Glu Asn Tyr Gly Lys Thr Leu Lys Ile Glu Asn Val Ser Tyr Gln Asp
    290                 295                 300

Lys Gly Asn Tyr Arg Cys Thr Ala Ser Asn Phe Leu Gly Thr Ala Thr
305                 310                 315                 320

His Asp Phe His Val Ile Val Glu Pro Pro Arg Trp Thr Lys Lys
                325                 330                 335

Pro Gln Ser Ala Val Tyr Ser Thr Gly Ser Asn Gly Ile Leu Leu Cys
                340                 345                 350

Glu Ala Glu Gly Glu Pro Gln Pro Thr Ile Lys Trp Arg Val Asn Gly
                355                 360                 365

Ser Pro Val Asp Asn His Pro Phe Ala Gly Asp Val Val Phe Pro Arg
        370                 375                 380

Glu Ile Ser Phe Thr Asn Leu Gln Pro Asn His Thr Ala Val Tyr Gln
385                 390                 395                 400

Cys Glu Ala Ser Asn Val His Gly Thr Ile Leu Ala Asn Ala Asn Ile
                    405                 410                 415

Asp Val Val Asp Val Arg Pro Leu Ile Gln Thr Lys Asp Gly Glu Asn
                420                 425                 430

Tyr Ala Thr Val Val Gly Tyr Ser Ala Phe Leu His Cys Glu Phe Phe
            435                 440                 445

Ala Ser Pro Glu Ala Val Val Ser Trp Gln Lys Val Glu Glu Val Lys
    450                 455                 460

Pro Leu Glu Gly Arg Arg Tyr His Ile Tyr Glu Asn Gly Thr Leu Gln
465                 470                 475                 480

Ile Asn Arg Thr Thr Glu Glu Asp Ala Gly Ser Tyr Ser Cys Trp Val
                485                 490                 495

Glu Asn Ala Ile Gly Lys Thr Ala Val Thr Ala Asn Leu Asp Ile Arg
                500                 505                 510

Asn Ala Thr Lys Leu Arg Val Ser Pro Lys Asn Pro Arg Ile Pro Lys
            515                 520                 525

Leu His Met Leu Glu Leu His Cys Glu Ser Lys Cys Asp Ser His Leu
    530                 535                 540

Lys His Ser Leu Lys Leu Ser Trp Ser Lys Asp Gly Glu Ala Phe Glu
545                 550                 555                 560

Ile Asn Gly Thr Glu Asp Gly Arg Ile Ile Ile Asp Gly Ala Asn Leu
                565                 570                 575

Thr Ile Ser Asn Val Thr Leu Glu Asp Gln Gly Ile Tyr Cys Cys Ser
                580                 585                 590

Ala His Thr Ala Leu Asp Ser Ala Ala Asp Ile Thr Gln Val Thr Val
            595                 600                 605

Leu Asp Val Pro Asp Pro Pro Glu Asn Leu His Leu Ser Glu Arg Gln
    610                 615                 620

Asn Arg Ser Val Arg Leu Thr Trp Glu Ala Gly Ala Asp His Asn Ser
625                 630                 635                 640

Asn Ile Ser Glu Tyr Ile Val Glu Phe Glu Gly Asn Lys Glu Glu Pro
                645                 650                 655

Gly Arg Trp Glu Glu Leu Thr Arg Val Gln Gly Lys Lys Thr Thr Val
                660                 665                 670

Ile Leu Pro Leu Ala Pro Phe Val Arg Tyr Gln Phe Arg Val Ile Ala
    675                 680                 685
```

```
Val Asn Glu Val Gly Arg Ser Gln Pro Ser Gln Pro Ser Asp His His
690                 695                 700
Glu Thr Pro Pro Ala Ala Pro Asp Arg Asn Pro Gln Asn Ile Arg Val
705                 710                 715                 720
Gln Ala Ser Gln Pro Lys Glu Met Ile Ile Lys Trp Glu Pro Leu Lys
                725                 730                 735
Ser Met Glu Gln Asn Gly Pro Gly Leu Glu Tyr Arg Val Thr Trp Lys
            740                 745                 750
Pro Gln Gly Ala Pro Val Glu Trp Glu Glu Thr Val Thr Asn His
        755                 760                 765
Thr Leu Arg Val Met Thr Pro Ala Val Tyr Ala Pro Tyr Asp Val Lys
770                 775                 780
Val Gln Ala Ile Asn Gln Leu Gly Ser Gly Pro Asp Pro Gln Ser Val
785                 790                 795                 800
Thr Leu Tyr Ser Gly Glu Asp Tyr Pro Asp Thr Ala Pro Val Ile His
                805                 810                 815
Gly Val Asp Val Ile Asn Ser Thr Leu Val Lys Val Thr Trp Ser Thr
            820                 825                 830
Val Pro Lys Asp Arg Val His Gly Arg Leu Lys Gly Tyr Gln Ile Asn
        835                 840                 845
Trp Trp Lys Thr Lys Ser Leu Leu Asp Gly Arg Thr His Pro Lys Glu
850                 855                 860
Val Asn Ile Leu Arg Phe Ser Gly Gln Arg Asn Ser Gly Met Val Pro
865                 870                 875                 880
Ser Leu Asp Ala Phe Ser Glu Phe His Leu Thr Val Leu Ala Tyr Asn
                885                 890                 895
Ser Lys Gly Ala Gly Pro Glu Ser Glu Pro Tyr Ile Phe Gln Thr Pro
            900                 905                 910
Glu Gly Val Pro Glu Gln Pro Thr Phe Leu Lys Val Ile Lys Val Asp
        915                 920                 925
Lys Asp Thr Ala Thr Leu Ser Trp Gly Leu Pro Lys Lys Leu Asn Gly
    930                 935                 940
Asn Leu Thr Gly Tyr Leu Leu Gln Tyr Gln Ile Ile Asn Asp Thr Tyr
945                 950                 955                 960
Glu Ile Gly Glu Leu Asn Asp Ile Asn Ile Thr Thr Pro Ser Lys Pro
                965                 970                 975
Ser Trp His Leu Ser Asn Leu Asn Ala Thr Thr Lys Tyr Lys Phe Tyr
            980                 985                 990
Leu Arg Ala Cys Thr Ser Gln Gly Cys Gly Lys Pro Ile Thr Glu Glu
        995                 1000                1005
Ser Ser Thr Leu Gly Glu Gly Ser Lys Gly Ile Gly Lys Ile Ser Gly
    1010                1015                1020
Val Asn Leu Thr Gln Lys Thr His Pro Ile Glu Val Phe Glu Pro Gly
1025                1030                1035                1040
Ala Glu His Ile Val Arg Leu Met Thr Lys Asn Trp Gly Asp Asn Asp
                1045                1050                1055
Ser Ile Phe Gln Asp Val Ile Glu Thr Arg Gly Arg Glu Tyr Ala Gly
            1060                1065                1070
Leu Tyr Asp Asp Ile Ser Thr Gln Gly Trp Phe Ile Gly Leu Met Cys
        1075                1080                1085
Ala Ile Ala Leu Leu Thr Leu Leu Leu Thr Val Cys Phe Val Lys
    1090                1095                1100
Arg Asn Arg Gly Gly Lys Tyr Ser Val Lys Glu Lys Glu Asp Leu His
```

```
                1105                1110                1115                1120
            Pro Asp Pro Glu Ile Gln Ser Val Lys Asp Glu Thr Phe Gly Glu Tyr
                            1125                1130                1135

Ser Asp Ser Asp Glu Lys Pro Leu Lys Gly Ser Leu Arg Ser Leu Asn
                        1140                1145                1150

Arg Asp Met Gln Pro Thr Glu Ser Ala Asp Ser Leu Val Glu Tyr Gly
                        1155                1160                1165

Glu Gly Asp His Gly Leu Phe Ser Glu Asp Gly Ser Phe Ile Gly Ala
                    1170                1175                1180

Tyr Ala Gly Ser Lys Glu Lys Gly Ser Val Glu Ser Asn Gly Ser Ser
            1185                1190                1195                1200

Thr Ala Thr Phe Pro Leu Arg Ala
                        1205

<210> SEQ ID NO 4
<211> LENGTH: 261
<212> TYPE: PRT
<213> ORGANISM: Homo sapiens

<400> SEQUENCE: 4

Met Ala Ser Pro Asp Trp Gly Tyr Asp Asp Lys Asn Gly Pro Glu Gln
            1               5                   10                  15

Trp Ser Lys Leu Tyr Pro Ile Ala Asn Gly Asn Asn Gln Ser Pro Val
                        20                  25                  30

Asp Ile Lys Thr Ser Glu Thr Lys His Asp Thr Ser Leu Lys Pro Ile
                    35                  40                  45

Ser Val Ser Tyr Asn Pro Ala Thr Ala Lys Glu Ile Ile Asn Val Gly
                50                  55                  60

His Ser Phe His Val Asn Phe Glu Asp Asn Asp Asn Arg Ser Val Leu
            65                  70                  75                  80

Lys Gly Gly Pro Phe Ser Asp Ser Tyr Arg Leu Phe Gln Phe His Phe
                        85                  90                  95

His Trp Gly Ser Thr Asn Glu His Gly Ser Glu His Thr Val Asp Gly
                        100                 105                 110

Val Lys Tyr Ser Ala Glu Leu His Val Ala His Trp Asn Ser Ala Lys
                    115                 120                 125

Tyr Ser Ser Leu Ala Glu Ala Ala Ser Lys Ala Asp Gly Leu Ala Val
                130                 135                 140

Ile Gly Val Leu Met Lys Val Gly Glu Ala Asn Pro Lys Leu Gln Lys
            145                 150                 155                 160

Val Leu Asp Ala Leu Gln Ala Ile Lys Thr Lys Gly Lys Arg Ala Pro
                        165                 170                 175

Phe Thr Asn Phe Asp Pro Ser Thr Leu Leu Pro Ser Ser Leu Asp Phe
                        180                 185                 190

Trp Thr Tyr Pro Gly Ser Leu Thr His Pro Pro Leu Tyr Glu Ser Val
                    195                 200                 205

Thr Trp Ile Ile Cys Lys Glu Ser Ile Ser Val Ser Ser Glu Gln Leu
                210                 215                 220

Ala Gln Phe Arg Ser Leu Leu Ser Asn Val Glu Gly Asp Asn Ala Val
            225                 230                 235                 240

Pro Met Gln His Asn Asn Arg Pro Thr Gln Pro Leu Lys Gly Arg Thr
                        245                 250                 255

Val Arg Ala Ser Phe
                        260
```

<210> SEQ ID NO 5
<211> LENGTH: 2386
<212> TYPE: PRT
<213> ORGANISM: Homo sapiens

<400> SEQUENCE: 5

```
Met Leu Arg Gly Pro Gly Pro Gly Leu Leu Leu Leu Ala Val Gln Cys
  1               5                  10                  15

Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
     50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380
```

```
Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
            405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
        450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
        610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
        690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
            725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
        770                 775                 780

Lys Tyr Ile Val Asn Val Tyr Gln Ile Ser Glu Asp Gly Glu Gln Ser
785                 790                 795                 800
```

```
Leu Ile Leu Ser Thr Ser Gln Thr Thr Ala Pro Asp Ala Pro Pro Asp
                805                 810                 815

Thr Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln Ile
    1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
                1045                1050                1055

Gln Pro Ala Ser Glu Tyr Thr Val Ser Leu Val Ala Ile Lys Gly Asn
            1060                1065                1070

Gln Glu Ser Pro Lys Ala Thr Gly Val Phe Thr Thr Leu Gln Pro Gly
        1075                1080                1085

Ser Ser Ile Pro Pro Tyr Asn Thr Glu Val Thr Glu Thr Thr Ile Val
    1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
                1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
        1155                1160                1165

Lys Val Val Thr Pro Leu Ser Pro Pro Thr Asn Leu His Leu Glu Ala
    1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
                1205                1210                1215

Gln Gly Asn Ser Leu Glu Glu Val Val His Ala Asp Gln Ser Ser Cys
```

```
                1220                1225                1230

Thr Phe Asp Asn Leu Ser Pro Gly Leu Glu Tyr Asn Val Ser Val Tyr
        1235                1240                1245

Thr Val Lys Asp Asp Lys Glu Ser Val Pro Ile Ser Asp Thr Ile Ile
    1250                1255                1260

Pro Ala Val Pro Pro Pro Thr Asp Leu Arg Phe Thr Asn Ile Gly Pro
1265                1270                1275                1280

Asp Thr Met Arg Val Thr Trp Ala Pro Pro Ser Ile Asp Leu Thr
            1285                1290                1295

Asn Phe Leu Val Arg Tyr Ser Pro Val Lys Asn Glu Glu Asp Val Ala
        1300                1305                1310

Glu Leu Ser Ile Ser Pro Ser Asp Asn Ala Val Val Leu Thr Asn Leu
    1315                1320                1325

Leu Pro Gly Thr Glu Tyr Val Val Ser Val Ser Ser Val Tyr Glu Gln
    1330                1335                1340

His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
            1365                1370                1375

His Trp Ile Ala Pro Arg Ala Thr Ile Thr Gly Tyr Arg Ile Arg His
        1380                1385                1390

His Pro Glu His Phe Ser Gly Arg Pro Arg Glu Asp Arg Val Pro His
    1395                1400                1405

Ser Arg Asn Ser Ile Thr Leu Thr Asn Leu Thr Pro Gly Thr Glu Tyr
    1410                1415                1420

Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
            1445                1450                1455

Val Ala Ala Thr Pro Thr Ser Leu Leu Ile Ser Trp Asp Ala Pro Ala
        1460                1465                1470

Val Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala Thr
    1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
            1525                1530                1535

Asn Tyr Arg Thr Glu Ile Asp Lys Pro Ser Gln Met Gln Val Thr Asp
        1540                1545                1550

Val Gln Asp Asn Ser Ile Ser Val Lys Trp Leu Pro Ser Ser Ser Pro
    1555                1560                1565

Val Thr Gly Tyr Arg Val Thr Thr Thr Pro Lys Asn Gly Pro Gly Pro
    1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
            1605                1610                1615

Pro Ser Gly Glu Ser Gln Pro Leu Val Gln Thr Ala Val Thr Asn Ile
        1620                1625                1630

Asp Arg Pro Lys Gly Leu Ala Phe Thr Asp Val Asp Val Asp Ser Ile
    1635                1640                1645
```

```
Lys Ile Ala Trp Glu Ser Pro Gln Gly Gln Val Ser Arg Tyr Arg Val
    1650                1655                1660

Thr Tyr Ser Ser Pro Glu Asp Gly Ile His Glu Leu Phe Pro Ala Pro
1665                1670                1675                1680

Asp Gly Glu Glu Asp Thr Ala Glu Leu Gln Gly Leu Arg Pro Gly Ser
        1685                1690                1695

Glu Tyr Thr Val Ser Val Val Ala Leu His Asp Asp Met Glu Ser Gln
        1700                1705                1710

Pro Leu Ile Gly Thr Gln Ser Thr Ala Ile Pro Ala Pro Thr Asp Leu
        1715                1720                1725

Lys Phe Thr Gln Val Thr Pro Thr Ser Leu Ser Ala Gln Trp Thr Pro
    1730                1735                1740

Pro Asn Val Gln Leu Thr Gly Tyr Arg Val Arg Val Thr Pro Lys Glu
1745                1750                1755                1760

Lys Thr Gly Pro Met Lys Glu Ile Asn Leu Ala Pro Asp Ser Ser Ser
        1765                1770                1775

Val Val Val Ser Gly Leu Met Val Ala Thr Lys Tyr Glu Val Ser Val
        1780                1785                1790

Tyr Ala Leu Lys Asp Thr Leu Thr Ser Arg Pro Ala Gln Gly Val Val
    1795                1800                1805

Thr Thr Leu Glu Asn Val Ser Pro Pro Arg Arg Ala Arg Val Thr Asp
    1810                1815                1820

Ala Thr Glu Thr Thr Ile Thr Ile Ser Trp Arg Thr Lys Thr Glu Thr
1825                1830                1835                1840

Ile Thr Gly Phe Gln Val Asp Ala Val Pro Ala Asn Gly Gln Thr Pro
        1845                1850                1855

Ile Gln Arg Thr Ile Lys Pro Asp Val Arg Ser Tyr Thr Ile Thr Gly
        1860                1865                1870

Leu Gln Pro Gly Thr Asp Tyr Lys Ile Tyr Leu Tyr Thr Leu Asn Asp
    1875                1880                1885

Asn Ala Arg Ser Ser Pro Val Val Ile Asp Ala Ser Thr Ala Ile Asp
    1890                1895                1900

Ala Pro Ser Asn Leu Arg Phe Leu Ala Thr Thr Pro Asn Ser Leu Leu
1905                1910                1915                1920

Val Ser Trp Gln Pro Pro Arg Ala Arg Ile Thr Gly Tyr Ile Ile Lys
        1925                1930                1935

Tyr Glu Lys Pro Gly Ser Pro Pro Arg Glu Val Val Pro Arg Pro Arg
        1940                1945                1950

Pro Gly Val Thr Glu Ala Thr Ile Thr Gly Leu Glu Pro Gly Thr Glu
    1955                1960                1965

Tyr Thr Ile Tyr Val Ile Ala Leu Lys Asn Asn Gln Lys Ser Glu Pro
    1970                1975                1980

Leu Ile Gly Arg Lys Lys Thr Asp Glu Leu Pro Gln Leu Val Thr Leu
    1985                1990                1995                2000

Pro His Pro Asn Leu His Gly Pro Glu Ile Leu Asp Val Pro Ser Thr
        2005                2010                2015

Val Gln Lys Thr Pro Phe Val Thr His Pro Gly Tyr Asp Thr Gly Asn
        2020                2025                2030

Gly Ile Gln Leu Pro Gly Thr Ser Gly Gln Gln Pro Ser Val Gly Gln
    2035                2040                2045

Gln Met Ile Phe Glu Glu His Gly Phe Arg Arg Thr Thr Pro Pro Thr
    2050                2055                2060
```

```
Thr Ala Thr Pro Ile Arg His Arg Pro Arg Pro Tyr Pro Pro Asn Val
2065                2070                2075                2080

Gly Glu Glu Ile Gln Ile Gly His Ile Pro Arg Glu Asp Val Asp Tyr
            2085                2090                2095

His Leu Tyr Pro His Gly Pro Gly Leu Asn Pro Asn Ala Ser Thr Gly
        2100                2105                2110

Gln Glu Ala Leu Ser Gln Thr Thr Ile Ser Trp Ala Pro Phe Gln Asp
    2115                2120                2125

Thr Ser Glu Tyr Ile Ile Ser Cys His Pro Val Gly Thr Asp Glu Glu
2130                2135                2140

Pro Leu Gln Phe Arg Val Pro Gly Thr Ser Thr Ser Ala Thr Leu Thr
2145                2150                2155                2160

Gly Leu Thr Arg Gly Ala Thr Tyr Asn Val Ile Val Glu Ala Leu Lys
            2165                2170                2175

Asp Gln Gln Arg His Lys Val Arg Glu Val Val Thr Val Gly Asn
        2180                2185                2190

Ser Val Asn Glu Gly Leu Asn Gln Pro Thr Asp Asp Ser Cys Phe Asp
    2195                2200                2205

Pro Tyr Thr Val Ser His Tyr Ala Val Gly Asp Glu Trp Glu Arg Met
2210                2215                2220

Ser Glu Ser Gly Phe Lys Leu Leu Cys Gln Cys Leu Gly Phe Gly Ser
2225                2230                2235                2240

Gly His Phe Arg Cys Asp Ser Ser Arg Trp Cys His Asp Asn Gly Val
            2245                2250                2255

Asn Tyr Lys Ile Gly Glu Lys Trp Asp Arg Gln Gly Glu Asn Gly Gln
        2260                2265                2270

Met Met Ser Cys Thr Cys Leu Gly Asn Gly Lys Gly Glu Phe Lys Cys
    2275                2280                2285

Asp Pro His Glu Ala Thr Cys Tyr Asp Asp Gly Lys Thr Tyr His Val
2290                2295                2300

Gly Glu Gln Trp Gln Lys Glu Tyr Leu Gly Ala Ile Cys Ser Cys Thr
2305                2310                2315                2320

Cys Phe Gly Gly Gln Arg Gly Trp Arg Cys Asp Asn Cys Arg Arg Pro
            2325                2330                2335

Gly Gly Glu Pro Ser Pro Glu Gly Thr Thr Gly Gln Ser Tyr Asn Gln
        2340                2345                2350

Tyr Ser Gln Arg Tyr His Gln Arg Thr Asn Thr Asn Val Asn Cys Pro
    2355                2360                2365

Ile Glu Cys Phe Met Pro Leu Asp Val Gln Ala Asp Arg Glu Asp Ser
2370                2375                2380

Arg Glu
2385

<210> SEQ ID NO 6
<211> LENGTH: 11
<212> TYPE: PRT
<213> ORGANISM: Homo sapiens

<400> SEQUENCE: 6

Glu Phe Gly Asn Thr Leu Glu Asp Lys Ala Arg
1               5                   10

<210> SEQ ID NO 7
<211> LENGTH: 10
<212> TYPE: PRT
<213> ORGANISM: Homo sapiens
```

```
<400> SEQUENCE: 7

Gly Thr Tyr Ser Thr Thr Val Thr Gly Arg
 1               5                  10

<210> SEQ ID NO 8
<211> LENGTH: 11
<212> TYPE: PRT
<213> ORGANISM: Homo sapiens

<400> SEQUENCE: 8

Gly Asp Leu Tyr Phe Ala Asn Val Glu Glu Lys
 1               5                  10

<210> SEQ ID NO 9
<211> LENGTH: 9
<212> TYPE: PRT
<213> ORGANISM: Homo sapiens

<400> SEQUENCE: 9

Val Leu Asp Ala Leu Gln Ala Ile Lys
 1               5

<210> SEQ ID NO 10
<211> LENGTH: 10
<212> TYPE: PRT
<213> ORGANISM: Homo sapiens

<400> SEQUENCE: 10

Ser Thr Thr Pro Asp Ile Thr Gly Tyr Arg
 1               5                  10

<210> SEQ ID NO 11
<211> LENGTH: 9
<212> TYPE: PRT
<213> ORGANISM: Escherichia coli

<400> SEQUENCE: 11

Gly Asp Phe Gln Phe Asn Ile Ser Arg
 1               5
```